United States Patent [19]

Numata et al.

[11] 4,264,595

[45] Apr. 28, 1981

[54] 7-[2-(2-IMINO-4-THIAZOLIN-4-YL)-2-(SYN)-HYDROXY-IMINOACETAMIDO]-CEPHALOSPORINS

[75] Inventors: Mitsuo Numata, Takatsuki; Isao Minamida, Kyoto; Susumu Tsushima, Suita, all of Japan

[73] Assignee: Takeda Chemical Industries, Ltd., Osaka, Japan

[21] Appl. No.: 807,409

[22] Filed: Jun. 17, 1977

[30] Foreign Application Priority Data

Sep. 8, 1976 [JP] Japan .................. 51-108101

[51] Int. Cl.³ .................. A61K 31/545; C07D 501/56
[52] U.S. Cl. .................. 424/246; 544/22; 544/25; 544/26; 544/27; 544/28; 544/30
[58] Field of Search .................. 544/27, 25; 424/246

[56] References Cited

U.S. PATENT DOCUMENTS

| | | | |
|---|---|---|---|
| 4,008,246 | 2/1977 | Ochiai et al. | 544/27 |
| 4,024,134 | 5/1977 | Gregson et al. | 544/27 |
| 4,024,137 | 5/1977 | Cook et al. | 544/27 |
| 4,033,950 | 7/1977 | Cook et al. | 544/27 |
| 4,092,477 | 5/1978 | Cook et al. | 544/26 |
| 4,093,803 | 6/1978 | Cook et al. | 544/27 |
| 4,098,888 | 7/1978 | Ochiai et al. | 544/22 |

*Primary Examiner*—Paul M. Coughlan, Jr.
*Attorney, Agent, or Firm*—Hubbell, Cohen, Stiefel & Gross

[57] ABSTRACT

Disclosed are 2-(syn)-hydroxyimino-acetamide derivatives of the formula:

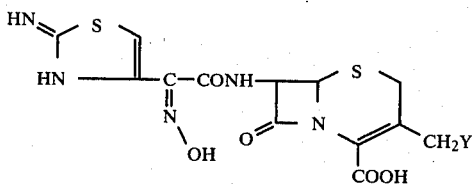

wherein Y is hydrogen, hydroxyl, an acyloxy, carbamoyloxy, a quaternary ammonium or a nitrogen-containing heterocyclic ring-substituted thio group; or pharmaceutically acceptable salts or esters thereof are useful as antibacterial agents. Also disclosed are processes for producing them.

33 Claims, No Drawings

7-[2-(2-IMINO-4-THIAZOLIN-4-YL)-2-(SYN)-HYDROXY-IMINOACETAMIDO]-CEPHALOSPORINS

This invention relates to novel antimicrobial agents useful for the treatment of diseases in animals including domestic fowls and human and particularly for the prevention or treatment of infectious diseases caused by Gram-positive and Gram-negative bacteria in those animals.

More concretely, this invention relates to 2-(syn)-hydroxyimino-acetamide derivatives of the formula:

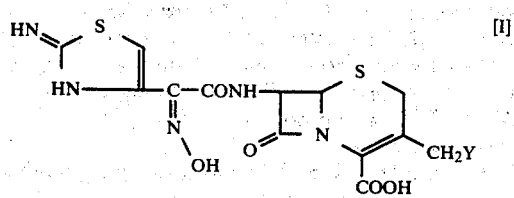

, wherein Y is hydrogen, hydroxyl, acyloxy, carbamoyloxy, quaternary ammonium or a nitrogen-containing heterocyclic thio, pharmaceutically acceptable salts and ester thereof. The invention also relates to processes for the production of the same.

Today several types of semi-synthetic cephalosporins known to possess broad antibacterial spectra are available on the market and have been clinically employed for the management of various infectious diseases. However, it has been reported that those agents are not practically active against all the pathogenic bacteria encountered in clinical situations. For example, it is known that certain strains of *Escherichia coli*, certain Citrobacter bacteria, a large majority of indole-positive pathogenic bacteria of the genus Proteus, the genus Enterobacter, the genus Serratia and the genus Pseudomonas are cephalosporin-resistant (Warren E. Wick, Cephalosporins and Penicillins; Chemistry and Biology, Chapter 11, edited by E. H. Flynn, Academic Press, 1972). Therefore, the search for new cephalosporins which are clinically effective against these pathogens is still being continued.

Under these circumstances, we have continued to create a vast number of new cephalosporin derivatives and to examine their pharmaceutical properties. We have now succeeded in synthesizing the above cephalosporin derivatives [I], their salts and esters and have found that these compounds are inhibitory against a wide variety of bacteria including Gram-positive bacteria and Gram-negative bacteria.

In particular, the beneficial features of the antimicrobial activity of the compounds of this invention are as follows. A preferred group of compounds of this invention not only displays practically sufficient activity against Gram-positive bacteria including *Staphylococcus aureus* but also exhibit activity against a broad spectrum of Gram-negative bacteria including *Escherichia coli*, *Klebsiella pneumoniae*, *Proteus vulgaris*, *Proteus mirabilis*, *Proteus morganii*, *Proteus rettgeri*, *Citrobacter freundii*, *Enterobacter cloacae* and *Serratia marcescens*. These superior characteristics are particularly pronounced with respect to activity against mutants of the aforementioned bacteria having β-lactamase (cephalosporinase).

Referring to formula [I], Y is hydrogen, hydroxyl, an acyloxy, carbamoyloxy, a quaternary ammonium and a nitrogen-containing heterocyclic thio.

The acyloxy is preferably a group of the formula —OT wherein T may for example be an aliphatic or aromatic carbonyl group having 2 to 10 carbon atoms such as acetyl, propionyl, benzoyl, etc. or reactive acyl groups such as those mentioned in German Patent Applications (OLS) 2607064 and 2619243. Those reactive acyl groups include, among others, 3-oxobutyryl, mandelyl, 3-carboxypropionyl, 2-carboxybenzoyl, 2-(N-carbethoxycarbamoyl)benzoyl, 2-(N-carbethoxysulfamoyl)benzoyl and 2-carboxy-3-(or6)-nitrobenzoyl. Although these reactive acyl groups do not contribute as much to the antimicrobial activity as does the acetyl group, they are highly reactive to water, an amine corresponding to the quaternary ammonium or a nitrogen-containing heterocyclic thio, as mentioned below.

The quaternary ammonium may be a substituted or unsubstituted pyridinium of the general formula:

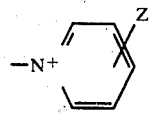

[wherein Z is hydrogen, an alkyl of one to four carbon atoms (e.g. methyl), carbamoyl, carboxyl, sulfo or an alkoxy of one to four carbon atoms (e.g. methoxy)], which includes pyridinium, a pyridinium substituted by carbamoyl (e.g. 3-carbamoylpyridinium, 4-carbamoylpyridinium etc.), a pyridinium substituted by sulfo (e.g. 4-sulfopyridinium, etc.), an alkylated pyridinium (e.g. 3-methylpyridinium, 4-methylpyridinium), a carboxypyridinium (e.g. 3-carboxypyridinium, 4-carboxypyridinium, etc.). The quarternary ammonium may also be quinolinium, picolinium, lutidinium etc. A preferable class of the quaternary ammonium is a pyridinium which may be substituted by a carbamoyl at the 4 position on the pyridinium ring. When the compound of the present invention contains a quaternary ammonium group, it may assume a betaine structure, for example:

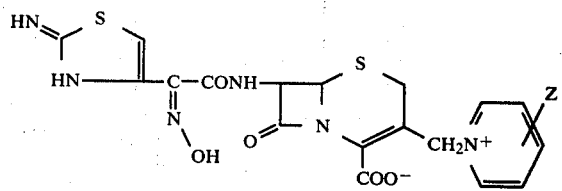

wherein Z is as defined above.

The nitrogen-containing heterocyclic thio group represented by Y may be a group of the formula: —S—Het wherein Het is a 5- or 6-membered heterocyclic group containing one to four nitrogen atoms and optionally further containing oxygen or a sulfur atom, and wherein said heterocylcic group may optionally have one or two substituents. As examples of such heterocyclic groups there may be mentioned six-membered heterocyclic groups including only one nitrogen atom (e.g. pyridyl, N-oxopyridyl), six-membered heterocyclic groups including two nitrogen atoms (e.g. pyrimidyl, pyridazinyl, N-oxopyridazinyl), five-membered heterocyclic groups including two nitrogen atoms (e.g. pyrazolyl, imidazolyl, etc.), five-membered heterocyclic groups including one nitrogen atom and one sulfur atom (e.g. thiazolyl), five-membered heterocyclic groups including two nitrogen atoms and one sulfur atom (e.g. 1,2,3-thiadiazolyl, 1,2,4-thiadiazolyl, 1,3,4-thiadiazolyl, 1,2,5-thiadiazolyl), five-membered heterocyclic groups including two nitrogen atoms and one oxygen atom (e.g. 1,2,3-oxadiazolyl, 1,2,4-oxadiazolyl, 1,3,4-oxadiazolyl, 1,2,5-oxadiazolyl), five-membered heterocyclic groups including three nitrogen atoms (e.g. 1,2,3-triazolyl, 1,2,4-triazolyl); and five-membered heterocyclic groups including four nitrogen atoms (e.g. 1H-tetrazolyl, 2H-tetrazolyl). Such heterocyclic groups may have, preferably, one or two substituents on the heterocyclic ring. The substituent is for example an alkyl of one to four carbon atoms (e.g. methyl, ethyl, propyl, isopropyl, butyl, isobutyl, etc.); a haloalkyl of one to four carbon atoms (e.g. trifluoromethyl); an alkoxy of one to four carbon atoms (e.g. methoxy, ethoxy, propoxy, isopropoxy, butoxy, etc.); halogen (e.g. chlorine, bromine, etc.); hydroxyl; mercapto; amino; carboxyl; carbamoyl; a residue of the formula: —X—Z$^1$ wherein X is an alkylene of one to four carbon atoms and Z$^1$ is hydroxyl, mercapto, amino, a mono- or di-alkylamino wherein the alkyl has one to four carbon atoms (e.g. dimethylamino, monoethylamino, etc.), guanyl, carboxyl, sulfo, carbamoyl, an alkoxycarbonyl wherein the alkyl has one to four carbon atoms (e.g. methoxycarbonyl, ethoxycarbonyl), a mono- or di-alkylcarbamoyl wherein the alkyl has one to four carbon atoms (e.g. N,N-dimethylcarbamoyl), an alkoxy of one to four carbon atoms (e.g. methoxy, ethoxy, n-propoxy), an alkylthio wherein the alkyl has one to four carbon atoms (e.g. methylthio), an alkylsulfonyl wherein the alkyl has one to four carbon atoms (e.g. methylsulfonyl) or an alkylcarbonyl wherein the alkyl has one to four carbon atoms (e.g. acetyl, n-propionyl); a residue of the formula: —S—Z$^2$ wherein Z$^2$ is an alkyl of one to four carbon atoms or the above-defined residue —X—Z$^1$; or a residue of the formula:

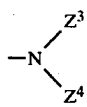

wherein each of Z$^3$ and Z$^4$ is an alkyl of one to four carbon atoms, the above-defined residue —X—Z$^1$, an alkoxycarbonyl wherein the alkoxy has one to four carbon atoms (e.g. methoxycarbonyl), an alkylcarbonyl wherein the alkyl has one to four carbon atoms (e.g. acetyl), carbamoyl or a mono- or di-alkylcarbamoyl wherein the alkyl has one to four carbon atoms (e.g. N,N-dimethylcarbamoyl), etc.

Thus, the substituent of the formula: —X—Z$^1$ on the heterocyclic group (Het) includes carboxymethyl, carbamoylmethyl, a mono- or di- alkyl(C$_{1-4}$)carbamoylmethyl (e.g. N,N-dimethylcarbamoylmethyl), hydroxyalkyl(C$_{1-4}$) (e.g. hydroxymethyl, 2-hydroxyethyl), an alkyl(C$_{1-4}$)-carbonyloxy-alkyl(C$_{1-4}$) (e.g. acetoxymethyl, 2-acetoxyethyl), an alkoxy(C$_{1-4}$)carbonylmethyl (e.g. methoxycarbonylmethyl), methylthiomethyl, methylsulfonylmethyl, aminoethyl, a mono- or di-alkyl(C$_{1-4}$)-amino-alkyl(C$_{1-4}$) (e.g. N,N-dimethylaminomethyl, N-methylaminoethyl, N,N-dimethylaminoethyl), guanylmethyl, guanylethyl, etc. The substituent of the formula: —S—Z$^2$ on the heterocyclic group (Het) includes methylthio, 2-hydryxyethylthio, 2-acetoxyethylthio, carboxymethylthio, an alkoxy(C$_{1-4}$)carbonylmethylthio (e.g. methoxycarbonylmethylthio), carbamoylmethylthio, N,N-dimethylcarbamoylthio, acetylmethylthio, 2-sulfoethylthio, etc.

The substituent of the formula:

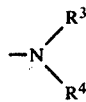

on the heterocyclic group (Het) includes a mono- or di-alkyl(C$_{1-4}$)amino (e.g. methylamino), a sulfoalkyl(C$_{1-4}$)amino (e.g. 2-sulfoethylamino), a hydroxyalkyl(C$_{1-4}$)amino (e.g. 2-hydroxyethylamino), a mono- or di-alkyl (C$_{1-4}$)amino-alkyl (C$_{1-4}$)amino (e.g. 2-dimethylaminoethylamino), an alkyl(C$_{1-4}$)carbonylamino (e.g. acetylamino), 2-dimethylaminoacetylamino, an alkoxy(C$_{1-4}$)carbonylamino (e.g. methoxycarbonylamino), etc.

An important class of the nitrogen-containing heterocyclic thio groups represented by Y is shown by the formulas:

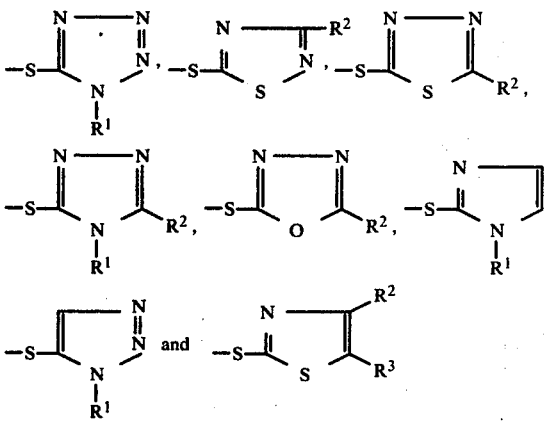

wherein R$_1$ is hydrogen or a residue of the formula: —(CH$_2$)$_n$P [in which n is an integer from 1 to 3 and P is hydrogen, hydroxyl, an alkoxy(C$_{1-4}$), an alkyl(C$_{1-4}$)thio, a residue of the formula: -COOR$^4$ (in which R$^4$ is hydrogen or an alkyl(C$_{1-4}$)), a residue of the formula:

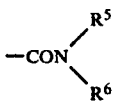

(in which each of R$^5$ and R$^6$ is hydrogen or an alkyl(C$_{1-4}$)) or a residue of the formula:

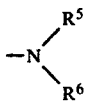

(in which each of R$^5$ and R$^6$ is as defined above)], and each of R$^2$ and R$^3$ is hydrogen, amino, carbamoyl, a residue of the formula: —NHCOOR$^7$(in which R$^7$ is an alkyl(C$_{1-4}$)), a residue of the formula: —S—(CH$_2$)$_n$Q (in which n is an integer from 1 to 3 and Q is carboxyl, hydroxyl, hydrogen or sulfo) or a residue of the formula: —(CH$_2$)$_n$P (in which each of n and P is as defined above). In the above, "alkyl($C_{1-4}$)" and "alkoxy($C_{1-4}$)" means "alkyl of one to four carbon atoms" and "alkoxy of one to four carbon atoms, respectively.

An important class of the compounds of the invention are those wherein the substituent Y is hydrogen, acetoxy, carbamoyloxy or the above-mentioned important class of nitrogen-containing heterocyclic thio groups.

The most preferred group of the Y substituents is acetoxy, carbamoyloxy, 3-substituted-1,2,4-thiadiazol-5-ylthio, 2-substituted-1,3,4-oxadiazol-5-ylthio, 1-substituted-imidazol-2-ylthio, 1-substituted-1H-tetrazol-5-ylthio, 2-substituted-1,3,4-thiadiazol-5-ylthio, 3,4-disubstituted-1,2,4-triazol-5-ylthio or 4-substituted-thiazol-2-ylthio, the substituent being methyl, carboxymethyl, hydroxymethyl, hydroxyethyl, carbamoylmethyl, 2-N,N-dimethylaminoethyl, methoxymethyl or ethoxycarbonylmethyl, the two substituents of 3,4-disubstituted-1,2,4-triazol-5-ylthio being the same or different. For the purpose of combatting bacteria the compound [I] may be employed as the free zwitterion compound or in other forms such as pharmaceutically acceptable salts, e.g. the salts of nontoxic cations such as sodium, potassium, etc.; the salts of basic amino acids such as arginine, ornithine, lysine, histidine, etc.; the salts of polyhydroxyalkylamines such as N-methylglucamine, diethanolamine, triethanolamine, trishydroxymethylamino trishydroxymethylaminomethane, etc.; the salts of inorganic acids such as hydrochloric acid, sulfuric acid, nitric acid, phosphoric acid, etc.; and the salts of organic acids (e.g. oxalic acid, fumaric acid, tartaric acid, etc.). The compound [I] or its above-mentioned salt may also be employed in the form of biologically active esters in the 4-carboxyl function, which ester derivatives would contribute to an elevated blood level and an increased duration of efficacy. Among the esters useful for the above purpose, there may be mentioned the group consisting of an alkoxy($C_{1-4}$)methyl ester, an alkoxy($C_{1-4}$)ethyl ester, an alkyl($C_{1-4}$)thiomethyl ester, an alkyl($C_{1-4}$)carbonyloxymethyl ester or an alkoxy($C_{1-4}$)carbonyloxyalkyl($C_{1-4}$) ester (e.g. alkoxy($C_{1-4}$)carbonyloxymethyl, etc.). More concretely, the esters include methoxyethyl ester, ethoxymethyl ester, isopropoxymethyl ester, α-methoxyethyl ester, α-ethoxyethyl ester, ethylthiomethyl ester, isopropylthiomethyl ester, pivaloyloxymethyl ester, α-acetoxybutyl ester and 1-(ethoxycarbonyloxy)ethyl ester, etc.

The compounds of this invention may assume a couple of different tautomeric forms by the tautomerization depicted below.

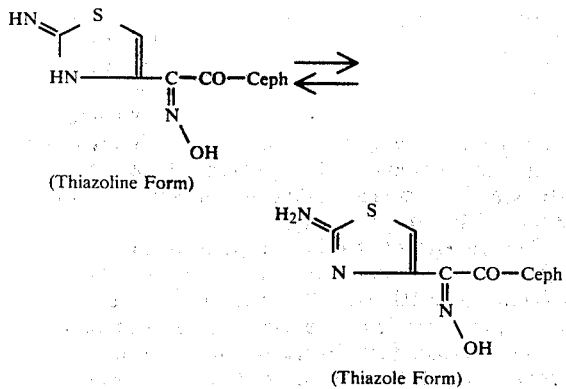

(Thiazoline Form)

(Thiazole Form)

[wherein Ceph is

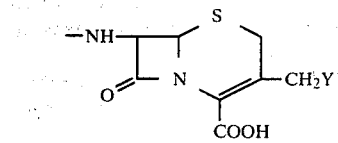

and wherein Y is defined hereinabove].

The form of existence of these types of compounds has been studied by many workers and the literature refers to the thiazoline form in several cases [G. J. Kruger and G. Gafner, Acta Cryst. B 27, 326 (1971); and J. M. Vandenbelt and L. Doub, J. Am. Chem. Soc. 66, 1633 (1944)] and the thiazole form in other cases [L. M. Werbel, Chem. & Ind. (1966), 1634].

However, based on various determinations, the compounds of this invention are thought to predominantly assume the thiazoline form since that particular form is stabilized by a contribution from the hydrogen bonding shown in the formula below.

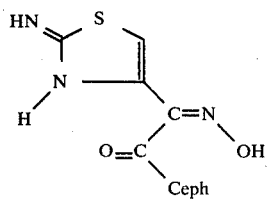

[wherein the symbol Ceph is as defined above]. However, as is true of any equilibrium-relation of this type, the above equilibrium is liable to shift either way in response to the various conditions under which the compounds of this invention may be placed, such as the pH and polarity of the solvent, temperature, kinds of substituents and other parameters. Therefore, the compounds of this invention may be designated by any of these alternative systems or corresponding nomenclatures thereof. In this specification and the claims appended thereto, however, all the compounds of the invention are designated by their thiazoline forms. This invention should, however, be construed to cover all the above tautomers.

The compounds of this invention are active against Gram-positive bacteria as well as Gram-negative bacteria, as mentioned above. They can be safely administered, as are the known cephalosporin drugs, in the form of powders or as a solution, suspension, ointment or other dosage forms as formulated with physiologically acceptable carriers, vehicles or excipients in the conventional manner. Said carriers, vehicles, excipients include water, physiological saline for injection or solution, and starch and lactose for powders. Among them, physiological saline is preferred.

For instance, the compounds of this invention can be employed as safe drugs for the prevention or therapy of infectious diseases caused by bacteria including pustulent diseases, respiratory tract infections, bile duct infections, intestinal infections, urinary tract infections and gyneco-obstetrical infections. The hosts to which the compounds are to be administered include human-beings or other warm-blooded animals including rat, mouse, dog, horse, etc.

For the therapy of the above diseases, for example, urinary tract infections, the following exemplary compounds, among other end product compounds of this invention, are preferably administered intramuscularly or intravenously at a daily dose level of about 1 to 20 mg per kg body weight in the case of adult humans, in three to four divided doses per day.

Sodium 7-[2-(2-imino-4-thiazolin-4-yl)-2-hydroxyiminoacetamido]-3-methyl-3-cephem-4-carboxylate (syn-isomer);

Sodium 7-[2-(2-imino-4-thiazolin-4-yl)-2-hydroxyiminoacetamido]-3-acetoxymethyl-3-cephem-4-carboxylate (syn-isomer);

Sodium 7-[2-(2-imino-4-thiazolin-4-yl)-2-hydroxyiminoacetoamido]-3-carbamoyloxymethyl-3-cephem-4-carboxylate (syn-isomer);

Sodium 7-[2-(2-imino-4-thiazolin-4-yl)-2-hydroxyiminoacetamido]-3-(1-methyltetrazol-5-yl)thiomethyl-3-cephem-4-carboxylate (syn-isomer);

7-[2-(2-imino-4-thiazolin-4-yl)-2-hydroxyiminoacetamido]-3-[1-(2-N,N-dimethylaminoethyl)tetrazol-5-yl]thiomethyl-3-cephem-4-carboxylic acid (syn-isomer);

Sodium 7-[2-(2-imino-4-thiazolin-4-yl)-2-hydroxyiminoacetamido]-3-[1-(3-N,N-dimethylaminopropyl)tetrazol-5-yl]thiomethyl-3-cephem-4-carboxylate (syn-isomer);

Sodium 7-[2-(2-imino-4-thiazolin-4-yl)-2-hydroxyiminoacetamido]-3-(1-carbamoylmethyltetrazol-5-yl)thiomethyl-3-cephem-4-carboxylate (syn-isomer);

Sodium 7-[2-(2-imino-4-thiazolin-4-yl)-2-hydroxyiminoacetamido]-3-[1-(2-hydroxyethyl)tetrazol-5-yl]thiomethyl-3-cephem-4-carboxylate (syn-isomer);

Sodium 7-[2-(2-imino-4-thiazolin-4-yl)-2-hydroxyiminoacetamido]-3-(1,3,4-thiadiazol-2-yl)thiomethyl-3-cephem-4-carboxylate (syn-isomer);

Sodium 7-[2-(2-imino-4-thiazolin-4-yl)-2-hydroxyiminoacetamido]-3-(2-methyl-1,3,4-thiadiazol-5-yl)thiomethyl-3-cephem-4carboxylate (syn-isomer);

7-[2-(2-imino-4-thiazolin-4-yl)-2-hydroxyiminoacetamido]-3-[2-82-N,N-dimethylaminoethyl)-1,3,4-thiadiazol-5-yl]thiomethyl-3-cephem-4-carboxylic acid (syn-isomer);

Sodium 7-[2-(2-imino-4-thiazolin-4-yl)-2-hydroxyiminoacetamido]-3-(2-hydroxymethyl-1,3,4-thiadiazol-5-yl)thiomethyl-3-cephem-4-carboxylate (syn-isomer);

Sodium 7-[2-(2-imino-4-thiazolin-4-yl)-2-hydroxyiminoacetamido]-3-(2-N,N-dimethylcarbamoylmethyl-1,3,4-thiadiazol-5-yl)thiomethyl-3-cephem-4-carboxylate (syn-isomer);

Sodium 7-[2-(2-imino-4-thiazolin-4-yl)-2-hydroxyiminoacetamido]-3-[2-(2-hydroxyethylthio-1,3,4-thiadiazol-5-yl]thiomethyl-3-cephem-4-carboxylate (syn-isomer);

Disodium 7-[2-(2-imino-4-thiazolin-4-yl)-2-hydroxyimino-acetamido]-3-(2-carboxymethyl-1,3,4-thiadiazol-5-yl)thiomethyl-3-cephem-4-carboxylate (syn-isomer);

7-[2-(2-imino-4-thiazolin-4-yl)-2-hydroxyiminoacetamido]-3-(3-methyl-1,2,4-thiadiazol-5-yl)thiomethyl-3-cephem-4-carboxylic acid (syn-isomer);

Sodium 7-[2-(2-imino-4-thiazolin-4-yl)-2-hydroxyimino-acetamido]-3-(1,2,3-triazol-4-yl)thiomethyl-3-cephem-4-carboxylate (syn-isomer);

Sodium 7-[2-(2-imino-4-thiazolin-4-yl)-2-hydroxyiminoacetamido]-3-(4-methyl-1,2,4-triazol-3-yl)thiomethyl-3-cephem-4-carboxylate (syn-isomer);

Sodium 7-[2-(2-imino-4-thiazolin-4-yl)-2-hydroxyiminoacetamido]-3-(3,4-dimethyl-1,2,4-triazol-5-yl)thiomethyl-3-cephem-4-carboxylate (syn-isomer);

Sodium 7-[2-(2-imino-4-thiazolin-4-yl)-2-hydroxyiminoacetamido]-3-(3-hydroxymethyl-4-methyl-1,2,4-triazol-5-yl)thiomethyl-3-cephem-4-carboxylate (syn-isomer);

Sodium 7-[2-(2-imino-4-thiazolin-4-yl)-2-hydroxyiminoacetamido]-3-(2-methyl-1,3,4-oxadiazol-5-yl)thiomethyl-3-cephem-4-carboxylate (syn-isomer);

Disodium 7-[2-(2-imino-4-thiazolin-4-yl)-2-hydroxyiminoacetamido]-3-(4-carboxymethylthiazol-2-yl)thiomethyl-3-cephem-4-carboxylate (syn-isomer);

Sodium 7-[2-(2-imino-4-thiazolin-4-yl)-2-hydroxyiminoacetamido]-3-(2-methoxymethyl-1,3,4-thiadiazol-5-yl)-thiomethyl-3-cephem-4-carboxylate (syn-isomer);

Sodium 7-[2-(2-imino-4-thiazolin-4-yl)-2-hydroxyiminoacetamide]-3-[2-(2-hydroxyethyl)-1,3,4-thiadiazol-5-yl]thiomethyl-3-cephem-4-carboxylate (syn-isomer);

Sodium 7-[2-(2-imino-4-thiazolin-4-yl)-2-hydroxyiminoacetamido]-3-(2-ethoxycarbonylmethyl-1,3,4-thiadiazol-5-yl)thiomethyl-3-cephem-4-carboxylate (syn-isomer).

On account of their antibacterial properties, the compounds of this invention may also be used as antiinfective agents or disinfectants for removing bacteria including the afore-mentioned or below-mentioned bacteria from surgical instruments or hospital rooms.

For example, surgical instruments are placed for 2 days in an aqueous solution containing 1000 μg /ml of any of the compounds of this invention for the above purpose.

With respect to the antibacterial properties of the present compounds, the compounds [I] and their salts have higher antibacterial activity than the esters of the compounds [I] as it is. However, the esters are hydrolyzed for example in the living tissue of the host, and the esters are converted into the compound [I] of their salts.

The compounds [I] of this invention, pharmaceutically acceptable salts or esters thereof are produced by procedures which are conventional per se.

The compond [I] or a pharmaceutically acceptable salt or ester thereof is produced by a method which comprises reacting a compound of the formula:

$$W-CH_2COCCONH-\underset{\underset{OH}{N}}{\overset{\parallel}{\underset{O}{\cdot}}}\begin{array}{c}S\\\diagup\diagdown\\-N\diagdown\diagup CH_2Y\\COOH\end{array}\quad [II]$$

wherein W is chlorine or bromine and Y is as defined above; or a salt or ester thereof with thioreau. The salts of the compounds [II] include acid addition salt (e.g. hydrochloric acid salts, sulfuric acid salt, nitric acid salt, etc.) at the basic function of the compound [II] and the basic addition salts (e.g. sodium salt, potassium salt, pyridine salt, triethylamine salt, etc.) at the acidic function of the compound [II]. The esters of the compounds [II] are those corresponding to the above-mentioned esters of the compounds [I].

The amount of thiourea relative to the compound [II], or salts or esters thereof is 1.0 to 5.0 moles per mole of compound [II], or a salt or ester thereof. The reaction is normally carried out by admixing the compound [II], a salt or ester thereof with thiourea at a temperature from 0° to 80° C. The reaction is preferably carried out in a solvent. The solvent is desirably a solvent that does not interfere with the reaction. Preferably, one of the so-called polar aprotic solvents such as dimethylformamide, dimethylacetamide, dimethylsulfoxide, acetonitrile, hexamethylphosphoramide, etc. or a mixture thereof is employed with advantage. The reaction time varies with the kind of the starting material, reaction temperature, kind of the solvent or other reaction conditions. However, the reaction goes to completion within a time ranging from 0.5 hour to 3 days.

The compounds of the present invention may be produced by another method i.e. by a nucleophilic displacement reaction. When Y in the formula [I] is hydroxyl, a quaternary ammonium or a nitrogen-containing heterocyclic thio, the compounds of the invention are also produced by a method which comprises reacting a compound of the formula:

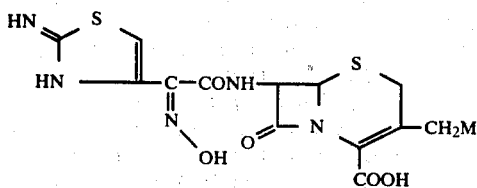

, wherein M is an acyloxy, or a salt or ester thereof with water, an amine corresponding to the quaternary ammonium or a nitrogen-containing heterocyclic thiol.

The kind of salts and esters of the compound [III] are the same as with those of the compound [II].

The acyloxy group M may for example be acetyloxy, 3-oxobutyryloxy, 3-carboxypropionyloxy, 2-carboxybenzoyloxy, mandelyloxy, 2-(N-carboethoxycarbamoyl)benzoyloxy, 2-(N-carboethoxysulfamoyl)benzoyloxy, 2- carboxy-3 (or 6)-nitrobenzoyloxy or the like. This transformation reaction, viewed only in the context of the 3-position of the cephem ring which is to be transformed, is a nucleophilic substitution reaction of the 3-acyloxy group and, as such, is essentially identical with the nucleophilic substitution reactions described in a number of prior art publications and patents (e.g. E. H. Flynn (ed.) "Cephalosporins and Penicillins", Chapter 4, Part 5, 151, 1972, Academic Press; Japanese Patent Publication 17936/1964; Japanese Patent Publication 26972/1964; and Japanese Patent Publication 11283/1968). Therefore, the above reaction can be carried out by one of those known methods or any method similar thereto.

As to the reaction between compound [III], its salt or ester and water, the reaction proceeds in accordance with the known hydrolysis. The hydrolysis reaction is normally carried out at a temperature between −20° C. and 50° C. The reaction proceeds faster in the presence of an inorganic base (e.g. sodium hydroxide) potassium hydroxide, etc.). The reaction goes to completion within 48 hours.

As to the reaction between the amine with the compound [III] or a salt thereof, the amine is one that corresponds to the quaternary ammonium. Thus the amine to be employed in the reaction includes pyridine compounds of the formula:

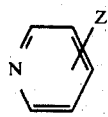

wherein Z is as defined above. The amount of the amine is 1.0 to 10 moles per mole of the compound [III] or a salt thereof. The reaction is carried out at a temperature between 0° C. and 100° C. The reaction is advantageously carried out in the presence of an organic or inorganic solvent. The solvent is for example water, deuterium oxide, dimethylformamide, dimethylacetamide, dioxane, acetone, methanol, ethanol, dimethylsulfoxide, acetonitrile, tetrahydrofuran etc. or mixtures thereof. The reaction goes to completion within 48 hours.

As to the reaction beteen the nitrogen-containing heterocylic thiol and the compound [III] or a salt thereof, the nitrogen-containing heterocyclic thiol is a thiol compound corresponding to the above-defined nitrogen-containing heterocyclic thio group. Thus, the nitrogen-containing heterocyclic thiol includes compounds of the formula:

HS—Het wherein Het is as defined above. The nitrogen-containing heterocyclic thiol may be used as the free thiol as such but, advantageously, is employed in the form of a salt such as an alkali metal salt, e.g. the sodium or potassium salt. The amount of the nitrogen-containing heterocyclic thiol relative to the compound [III] or a salt thereof is 1.0 to 5.0 moles per mole of the compound [III] or a salt thereof. This reaction is preferably conducted in a solvent. The solvent may for example be water, deuterium oxide or an organic solvent which is readily miscible with water and does not react with the starting materials, e.g. dimethylformamide, dimethylacetamide, dioxane, acetone, alcohol, acetonitrile, dimethylsulfoxide, tetrahydrofuran, etc. While the reaction temperature and time depend upon the starting material and solvent, among other factors, the reaction is generally carried out at an appropriate temperature from 0° to 100° C. for an appropriate time ranging from a few minutes to several days. The reaction is conducted in the neighborhood of neutrality, i.e. between pH 2 and pH 8 and, preferably, in the range of pH 5 to 8. The reaction may optionally be conducted more smoothly by incorporating in the reaction system, a quaternary ammonium salt having surface active properties, such as trimethylbenzylammonium bromide, triethylbenzylammonium bromide or triethylbenzylammonium hydroxide. Moreover, advantageous results are obtained when the reaction is conducted in an atmosphere of an inert gas, e.g. nitrogen, so as to prevent atmospheric oxidation.

The compounds of this invention may also be produced by another well known method, i.e. the acylation reaction method.

The compounds of this invention are produced by a method which comprises reacting a compound of the formula:

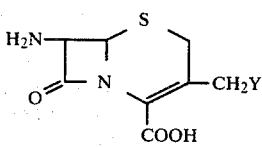

wherein Y is as defined above, or a salt or ester thereof with an acylating agent derived from a syn-isomeric carboxylic acid of the formula:

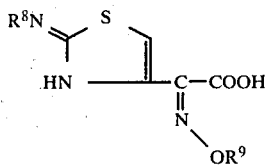

[V]

wherein $R^8$ is hydrogen or a protecting group and $R^9$ is hydrogen or a protecting group. The kind of salt or ester of the compound [IV] is the same as that of compound [II]. The protecting group represented by $R^8$ is an easily cleavable protecting group which is well known in the field of peptide chemistry. Thus the protecting group $R^8$ includes formyl, an alkyl($C_{1-4}$)carbonyl group (e.g. acetyl, propionyl, etc.), a substituted alkyl($C_{1-4}$)carbonyl group (e.g. chloroacetyl etc.), an alkoxy($C_{1-4}$)carbonyl group (e.g. t-butoxycarbonyl, etc.), an alkoxy($C_{1-4}$)alkyl($C_{1-4}$)carbonyl group (e.g. methoxyacetyl), methoxypropionyl, etc.), a substituted alkoxy($C_{1-4}$)carbonyl group (e.g. trichloroethoxycarbonyl, etc.), an aralkyl($C_{7-10}$)oxycarbonyl group (e.g. benzyloxycarbonyl, etc.), or a substituted aralkyl($C_{7-10}$)oxycarbonyl group (e.g. p-nitrobenzyloxycarbonyl, etc.), or a proton.

The protecting group $R^9$ is a an easily cleavable protecting group well known among chemists, which can be removed under mild conditions. The protecting group $R^9$ is exemplified by an acyl group such as formyl, acetyl, chloroacetyl, trifluoroacetyl, methoxyacetyl, phenoxyacetyl, benzoyl, benzoylformyl, p-nitrobenzoyl, ethoxycarbonyl, $\beta,\beta,\beta$-trichloroethoxycarbonyl, $\beta, \beta, \beta$-tribromoethoxycarbonyl, p-nitrophenoxycarbonyl, and a substituted alkyl such as a tetrahydrothiofuranyl, methoxy, methoxytetrahydropyranyl, etc. tetrahydropyranyl and 2-methoxyethoxymethyl, and also by a silyl group such as trimethylsilyl, dimethyl-t-butylsilyl, etc.

In this process, the compound [V] is employed, either as a free compound [V], its salt or in the form of a reactive derivative, as an acylating agent for the acylation of the amino group in the 7-position of compound [IV] or a salt or ester thereof. Thus, the free acid [V], an alkali or alkaline earth metal salt of the free acid [V] (e.g. sodium, potassium or calcium salt) an organic amine salt of the free acid [V] (e.g. trimethylamine or pyridine salt) or a reactive derivative thereof [such as a corresponding acid halide (e.g. acid chloride or acid bromide), acid anhydride, mixed acid anhydride, active amide, active ester or the like] is subjected to the aforementioned reaction. As examples of said active ester there may be mentioned the p-nitrophenyl ester, 2,4-dinitrophenyl ester, pentachlorophenyl ester, N-hydroxysuccinimide ester and N-hydroxyphthalmide ester. As examples of said mixed acid anhydride there may be mentioned mixed acid anhydride with a carbonic acid monoester (e.g. carbonic acid monomethyl ester or carbonic acid monisobutyl ester) and a mixed acid anhydride with a lower alkanoic acid having one to five carbon atoms which may be substituted by halogen (e.g. pivalic acid or trichloroacetic acid). Where the carboxylic acid [V] is employed as the free acid or in the form of a salt, there is employed a suitable condensing agent. As examples of said condensing agent may be mentioned N,N'-di-substituted carbodiimides, e.g. N,N'-dicyclohexyl-carbodiimide; azolides, e.g. N,N'-carbonylimidazole and N,N'-thionyldiimidazole; dehydrating agents, e.g. N-ethoxycarbonyl-2-ethoxy-1,2- dihydroquinoline, phosphorus oxychloride and alkoxyacetylene; 2-halogenopyridinium salts (e.g. 2-chloropyridiniummethyl iodide, 2-fluoropyridiniummethyl iodide) and the like. Where such a condensing agent is employed, it is presumed that the reaction proceeds via the reactive derivative of the carboxylic acid [V] coupled with the condensing agent.

This reaction between the compound [IV], or a salt or ester thereof with the acylating agent proceeds readily under per se known conditions. For example, the reaction may be conducted under conditions analogous to those disclosed in German Patent Application (OLS) No. P 2461478. The reaction is usually conducted in a suitable inert solvent. As examples of such a solvent there may be mentioned halogenated hydrocarbons, e.g. chloroform, methylene chloride, etc.; ethers, e.g. tetrahydrofuran, dioxane, etc.; dimethylformamide; dimethylacetamide; acetone; water and mixtures thereof. The proportion of said acylating agent is normally within the range of about 1 to 5, preferably 1 to 2, molar equivalents, based on the compound [IV] or a salt or ester thereof. This reaction is generally carried out at a temperature in the range of $-50°$ to $+40°$ C. The reaction time is one to ten hours, preferably one to three hours. Following the acylation reaction, the protective groups $R^8$ or/and $R^9$ may be removed, if desired. The removal of the protective groups $R^8$ or/and $R^9$ may be generally accomplished by procedures known per se [e.g. by the procedure described in Japanese Patent Application Laid Open No. 52083/1975 and Pure and Applied Chemistry, 7, 335(1963)] or a procedure analogous thereto.

Thus, for example, t-butoxycarbonyl represented by $R^8$ may be removed by treatment with an aqueous solution of an acid (e.g. hydrogen chloride, sulfuric acid etc.), and monochloroacetyl represented by $R^8$ may be removed by treatment with thiourea. Formyl or trifluoroacetyl represented by $R^9$ may be removed by treatment with potassium hydrogen carbonate in aqueous methanol, and tetrahydropyranyl represented by $R^9$ may be removed by treatment with dilute hydrochloric acid. The removal of the protecting group is carried out under conditions known per se.

When the end product [I] is produced in the form of the free acid, it can be converted into a pharmaceutically acceptable salt thereof by a per se conventional procedure.

When the end product of the present invention is obtained in the form of a salt, it can be converted into the free form or any other salts by a per se well known procedure.

When the end product of the present invention is obtained in the form of free carboxylic acid or its salt at the 4 position, it may be esterified into an ester in accordance with conventional means, the kind of ester having been detailedly defined hereinabove. More concretely, the ester is produced by a method, which comprises reacting a compound [I] or a salt or reactive derivative thereof with a compound of the formula:

$$HO-R^{10} \qquad [VI]$$

, in which $R^{10}$ is an ester residue, or a reactive derivative thereof. The kind of salt of compound [I] includes that of compound [II], and the kind of reactive derivative of compound [I] is the same as that of compound [V]. The reactive derivative of the compound [VI] includes a compound of the formula: $Hal-R^{10'}$[VI'] in which Hal is halogen and $R^{10'}$ is an alkoxy$(C_{1-4})$methyl, an alkoxy$(C_{1-4})$ethyl, an alkyl$(C_{1-4})$thiomethyl, an alkyl$(C_{1-4})$carbonyloxymethyl or an alkoxy$(C_{1-4})$carbonyloxyalkyl$(C_{1-4})$. Examples of these groups have been mentioned in detail hereinabove with reference to compound [I].

The symbol Hal means chlorine, fluorine, bromine or iodine, and Hal is preferably iodine or bromine.

Thus the compound of the formula [VI'] is exemplified by methoxymethyl chloride, methylthiomethyl chloride, chloromethyl acetate, bromomethyl acetate, bromomethyl pivalate, iodomethyl pivalate, iodomethyl ethoxycarbonate, etc.

When the starting compound [I] is used in the free carboxylic acid form at the 4 position, it is preferable to carry out the reaction in the presence of a base. The base is for example, an inorganic base such as sodium hydrogen carbonate, potassium hydrogen carbonate, lithium carbonate, sodium carbonate, potassium carbonate etc. or an organic base such as dicycloyhexylamine, morpholine, N-ethylaniline, N-N-diethylaniline, N-methylmorpholine, pyridine, triethylamine, etc.

The reaction may be carried out in a solvent such as acetonitrile, N,N-dimethylformamide, N,N-dimethylacetamide, N,N-dimethylformamide, dichloromethane, chloroform, dimethylsulfoxide, diethyl ether, tetrahydrofuran, acetone, methyl ethyl ketone, liquid sulfuric anhydride. Among them, dimethylformamide, acetone, acetonitrile and liquid sulfuric anhydride are preferred.

The amount of the base is usually one equivalent relative the starting compound [I] or a salt thereof.

The reaction is preferably carried out at a temperature between $-20°$ C. and $20°$ C. When liquid sulfuric anhydride is used as the solvent, the reaction temperature is preferably a temperature in a range from $-20°$ C. to $-10°$ C.

The reaction time varies with the kind of starting materials, reaction temperature, the kind of solvent etc., but it is usually from 10 minutes to 120 hours.

After any of the reactions which produce the compounds of the present invention, the desired compound is isolated from the reaction mixture in accordance with per se known procedures. The compounds of the present invention may be purified by known techniques. Such procedures or techniques are exemplified by extraction, pH adjustment, concentration, crystallization, recrystallization, chromatography, etc.

The compound [I], or a salt or ester thereof of this invention has a hydroxyl group in the syn configuration relative to the acetamide group (i.e. —CONH—) at the 7 position. However, there are cases in which the formation of compound [I] is accompanied by the formation of the anti isomer of the formula:

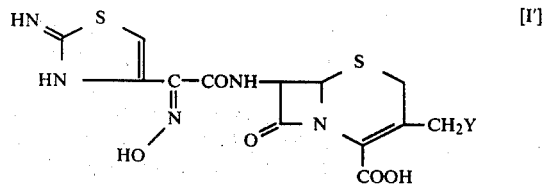

[I']

, wherein Y is as defined above, a corresponding salt or ester thereof, even if only the corresponding syn-isomeric starting compound is used. However, in the method comprising the reaction between (1) compound [III] or a salt thereof and (2) water, the amine or the nitrogen-containing heterocyclic thio or the method comprising the reaction between (1) the compound [II], a salt or ester thereof and (2) thiourea when the starting material [II], [III] or a salt or ester thereof is a substantially pure synisomer, the yield of the anti isomer [I'] does not exceed 10% of that of the compound [I].

Of course, when syn isomeric starting compound [II], [III] or [V] is employed in combination with the corresponding anti isomeric compound, the reaction mixture contains the compounds [I] and [I'] (i.e. syn and anti isomeric mixture). This is of course also true in the case where a salt or ester of the compound [II], [III] or [V] is employed as the starting material. The desired syn isomer [I], or a salt or ester thereof is easily separated or isolated by well known means such as chromatography, fractional crystallization etc.

The compound [II], or a salt or ester thereof is produced by the following scheme, by the methods described in Japanese Patent Laid-Open Application No. 95293/1975, No. 11093/1975 and No. 56487/1976 or Japanese Patent Application No. 1274/1976 or by any method similar to any of those methods, for instance:

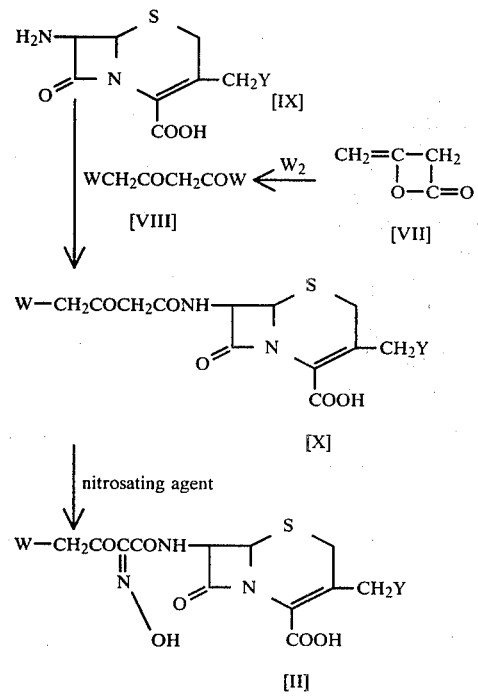

wherein each of W and Y is as defined above.

Firstly, bromine or chlorine represented by $W_2$ is reacted with diketene, e.g. of the formula [VII], the amount of bromine or chlorine being equimolar to the diketene. Then, the thus produced compound [VIII] is reacted with compound [IX] or a salt or ester thereof in a manner known per se to produce compound [X], a salt ester thereof. The compound [IX], or a salt or ester thereof can be produced by any of the known methods, for example, by the method described in Japanese Patent Application Laid-Open No. 11782/1976, German Patent Application Laid-Open No. P 2607064 and No. P 2619243 or any other methods analogous thereto. Thus, compound [IX] or a salt or ester thereof can be obtained by converting the 3-position substituent of a 7-acylamino-3-acetoxymethyl-3-cephem-4-carboxylic acid or 7-acylamino-3-hydroxymethyl-3-caphem-4-carboxylic acid, or a salt or ester thereof to a desired —CH₂Y group and, then, removing the 7-acyl group, or alternatively by subjecting an 7-amino-3-activated acyloxymethyl-3-cephem-4-carboxylic acid (of which the activated acyloxy group is described hereinabove) or a salt thereof directly to a nucleophilic substitution reaction with water, an amine corresponding to the quaternary ammonium or the nitrogen-containing heterocyclic thiol.

Then the compound [X], or a salt or ester thereof is reacted with a nitrosating agent to obtain the compound [II], or a salt or ester thereof. As to the salt of the compound [X], for example, where a basic group is present in the substituent Y of compound [X] (e.g. where Y is 1-(2-N,N-dimethylaminoethyl)-1H-tetrazol-5-ylthio), compound [X] may be reacted as an acid salt at that basic function, for example the salt of a mineral acid (e.g. hydrochloric acid, sulfuric acid or phosphoric acid) or the salt of an organic acid (e.g. oxalic acid, or p-toluenesulfonic acid). Where a strongly acidic group is present in the substituent Y of compound [X] (e.g. where Y is 2-(2-sulfoethylamino)-1,3,4-thiadiazol-5-ylthio), compound [X] may be reacted as an inorganic or organic salt in that acidic function, e.g. the salt of an alkali metal or alkaline earth metal (e.g. lithium, sodium or potassium) or an organic basic salt (e.g. triethylamine salt).

As the nitrosating agent, there may normally be employed one of such agents such as nitrous acid, nitrous acid esters such as methyl nitrite, ethyl nitrite, amyl nitrite, etc. and nitrosyl chloride, for instance. Nitrous acid may be used as it is produced in the reaction system by the reaction of an alkali metal nitrite with an acid, e.g. hydrochloric acid or acetic acid.

The nitrosation reaction, i.e. the reaction between compound [X], or a salt or ester thereof and the nitrosating agent is preferably carried out in a solvent. Any solvent which does not interfere with the reaction can be employed. Normally, dioxane, acetonitrile, tetrahydrofuran, water, acetic acid or an appropriate mixture of such solvents is employed. This reaction is hastened by the presence of an acid. Most conveniently this acid is hydrochloric acid or acetic acid. The amount of the acid is one mole or more per mole of compound [I]. Normally the nitrosation reaction is preferably carried out at room temperature (25°–35° C.) or under cooling or slight heating. Thus, the reaction is carried out at a temperature between −20° C. and 50° C.

By this nitrosation reaction, the hydroxime compound [II] having a syn-configuration with respect to the acylamide group can be obtained with high efficiency. Under certain circumstances there is obtained a stereoisomer having an anti-configuration as shown by the formula [II'], in some minor amount, together with the aforesaid compound [II] but, in many cases, the yield of the stereoisomer [II'] does not exceed 10 percent of the amount of [II].

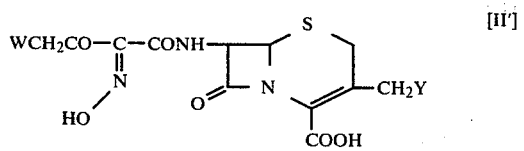

[wherein W and Y are as hereinbefore defined].

This is a particularly advantageous feature of this invention which is directed to the production of a compound [I] which has a syn-configuration as does the compound [II]. The compound [II] thus obtained can be isolated and purified by conventional procedures such as solvent extraction, pH adjustment, phase transfer, crystallization, recrystallization, chromatography, etc.

The nitrogen-containing heterocyclcic thiol (e.g. the above mentioned compound of the formula: HS-Het in which Het is as defined above) can be produced (1) by the per se known methods described, for example, in Chapter 5 of Heterocyclic Chemistry (A. R. Katritzky and J. M. Lagowsky, John Willey and Sons, 1960), Chapter 1 of Heterocylic Compounds, Vol. 8 (R. C. Elderfield, John Willey and Sons, 1967), Advances in Heterocyclic Chemistry, Vol. 9 (A. R. Katritzky and A. J. Boulton, Academic Press, 1968, pp. 165 to 209, and Dai Yuki Kagaku (Munio Kotake (ed.), Asakura Shoten, Vol. 15 or by methods analogous to those known methods, or (2) by subjecting of the nitrogen-containing heterocyclic thiol, whether known or as produced by any of the above methods (1), to a per se known chemical modification reaction or reactions of any functional group or groups other than the thiol group.

The compound of the formula [V] or a salt thereof is produced by a per se known method. Thus, the compound [V] or a salt thereof is produced by a method which comprises subjecting a syn-isomeric compound of the formula:

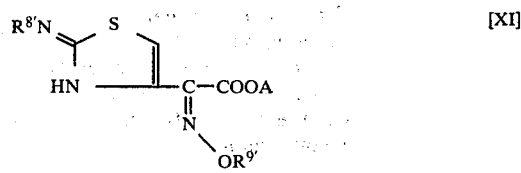

, wherein R⁸' is hydrogen or a protecting group, R⁹' is hydrogen or a protecting group and A is an ester residue, or a salt thereof to a deesterification reaction. The ester residue A is exemplified by an alkyl($C_{1-4}$) (e.g. methyl, ethyl, n-propyl, i-propyl, t-butyl, etc.), or an alkyl($C_{1-4}$) substituted by phenyl (e.g. benzhydryl etc.).

The deesterification reaction is carried out by a per se conventional means including hydrolysis, hydrogenolysis, acid cleavage, etc. The preferred mode of deesterification is to bring the compound [XI] or a salt thereof into contact with a mixture containing trifluoroacetic acid and anisole. The amount of each of trifluoroacetic acid and anisole is in excess relative to the compound [XI] or its salt. The reaction is carried out at a temperature between −20° C. and 30° C., and the reaction usually goes to completion within 5 hours. If desired, the compound [XI] may be used in combination with the corresponding anti isomer or its salt. After the reaction, the desired compound [V] or its salt may be isolated or purified by a per se conventional means such as concentration, crystallization, chromatography, etc. However, the reaction mixture containing the compound [V] or its salt may be subjected to the next reaction without purification or isolation. The above-mentioned reactive derivatives of the compound [V] are produced by a per se known methods from the compound [V] or its salt.

The compound [XI] or its salt is produced by a per se known method or methods described in the reference examples below.

The present invention is illustrated in further detail below with reference to the examples, but it is to be understood that the examples are solely for the purpose of illustration and not to be construed as limitations of the invention, and that many variations may be resorted to without departing from the spirit and scope of the invention.

The percentages given are all on a weight basis except where specifically otherwise defined. The NMR spectra given in the examples were measured using a Varian Model XL-100A (100MHz) or T-60 (60 MHz) spectrometer with tetramethylsilane as the internal or external reference and all δ values are in ppm. The symbol s stands for a singlet, d a doublet, dd a double doublet, t a triplet, q a quartet, m a multiplet, and J a coupling constant.

EXPERIMENT

The tables given below set forth the minimal inhibitory concentrations (MIC) of some typical compounds [I] of this invention as obtained in the working examples against various bacteria in comparison with the comparable MIC data on some of the cephalosporins heretofore commercially available and clinically accepted (e.g. The New England Journal of Medicine 294, 24 (1976) and Journal of Pharmaceutical Science 64 1899 (1975), i.e.

Cephalothin [sodium 7-(2-thienylacetamido)-3-acetoxymethyl-3-cephem-4-carboxylate];
Cephaloridine [7-(2-thienylacetamido)-3-(1-pyridyl)-methyl-3-cephem-4-carboxylic acid betaine]; and
Cefazolin [sodium 7-(1H-tetrazol-1-yl)acetamido-3-(2-methyl-1,3,4-thiadiazol-5-yl)thiomethyl-3-cephem-4-carboxylate].

The therapeutic efficacies of several representative compounds [I] of this invention and of cephaloridine on infected mice are also set forth in the tables.

(a) Minimal inhibitory concentrations (Table 1 and 2)
Method: Agar serial dilution
Medium: TSA
Inoculum size: $10^7$/ml

TABLE 1

| Test compound | Gram-positive bacteria | | Gram-negative bacteria | | | | | | |
|---|---|---|---|---|---|---|---|---|---|
| | Staphylococcus aureus 209P | Staphylococcus aureus 1840 | Escherichia coli NIHJ JC-2 | Escherichia coli 0-111 | Escherichia coli T-7 | Klebsiella pneumoniae DT | Klebsiella pneumoniae GN-3835 | Serratia marcescens IFO 12648 | Serratia marcescens TN24 |
| Cephalothin | 0.20 | 0.39 | 12.5 | 3.13 | 100 | 1.56 | 12.5 | >100 | >100 |
| Cephaloridine | 0.05 | 0.39 | 3.13 | 1.56 | >100 | 1.56 | 12.5 | >100 | >100 |
| Cefazolin | 0.39 | 1.56 | 1.56 | 1.56 | 50 | 1.56 | 6.25 | >100 | >100 |
| Example 5 | 0.39 | 0.39 | 0.024 | ≦0.012 | 0.39 | ≦0.012 | 0.05 | 6.25 | 1.56 |
| Example 12 | 0.39 | 0.78 | 0.05 | ≦0.012 | 0.78 | 0.024 | 0.10 | 0.78 | 0.39 |
| Example 16 | 0.39 | 0.78 | 0.10 | 0.024 | 1.56 | 0.05 | 0.20 | 3.13 | 0.78 |
| Example 15 | 0.78 | 0.78 | 0.024 | ≦0.012 | 0.39 | 0.024 | 0.05 | 0.78 | 0.78 |
| Example 13 | 0.78 | 0.78 | 0.10 | 0.05 | 0.78 | 0.05 | 0.20 | 12.5 | 1.56 |
| Example 14 | 0.39 | 0.78 | 0.39 | 0.20 | 6.25 | 0.20 | 0.78 | 6.25 | 0.78 |
| Example 17 | 0.39 | 0.39 | 0.39 | 0.20 | 25 | 0.20 | 1.56 | 1.56 | 0.78 |
| Example 26 | 0.78 | 0.78 | 0.05 | 0.024 | 0.39 | 0.024 | 0.05 | 12.5 | 1.56 |

TABLE 2

| Test compound | Gram-negative bacteria | | | | | | | | |
|---|---|---|---|---|---|---|---|---|---|
| | Proteus vulgaris IFO 3988 | Proteus vulgaris GN4413 | Proteus mirabilis GN4359 | Proteus morganii IFO3168 | Proteus rettgeri TN338 | Proteus rettgeri GN4733 | Enterobacter cloacae TN1282 | Citrobacter freundii GN99 | Citrobacter freundii GN1706 |
| Cephalothin | 1.56 | >100 | 3.13 | >100 | 1.56 | >100 | >100 | 25 | >100 |
| Cephaloridine | 6.25 | >100 | 6.25 | >100 | 1.56 | >100 | >100 | 50 | >100 |
| Cefazolin | 3.13 | >100 | 6.25 | 100 | ≦0.2 | 100 | >100 | 12.5 | >100 |
| Example 5 | 0.05 | 12.5 | 0.05 | 0.20 | ≦0.012 | 0.024 | 6.25 | 0.05 | 0.10 |
| Example 12 | 0.05 | 6.25 | 0.10 | 0.024 | ≦0.012 | 0.05 | 1.56 | 0.05 | 0.10 |
| Example 16 | 0.10 | 6.25 | 0.20 | 0.05 | ≦0.012 | 0.10 | 6.25 | 0.10 | 0.20 |
| Example 15 | 0.05 | 3.13 | 0.10 | 0.024 | ≦0.012 | 0.10 | 1.56 | 0.05 | 0.05 |
| Example 13 | 0.10 | 50 | 0.10 | 0.20 | ≦0.012 | 0.20 | 25 | 0.39 | 0.78 |
| Example 14 | 0.10 | 1.56 | 0.39 | 0.20 | 0.024 | 0.39 | 6.25 | 0.39 | 0.78 |
| Example 17 | 0.39 | 3.13 | 0.39 | 0.39 | 0.05 | 0.20 | 12.5 | 0.20 | 0.78 |
| Example 26 | 0.10 | 50 | 0.05 | 0.39 | ≦0.012 | 0.024 | 12.5 | 0.05 | 0.10 |

(b) Therapeutic effects on infected mice (Table 3 and Table 4)
Test animal: Male mouse, ICR/SLC
A group of five animals was employed per drug.
Route of infection: Intraperitoneal
Infectious bacteria: *Escherichia coli* 0-111
Period of observation: 7 days
Method of administration: Test compound (1 mg, 10 mg, 100 mg or 200 mg) was dissolved in sterile saline solution (100 ml) and 0.2 ml of the solution was administered subcutaneously as a single dose immediately after infection. Two fold dilutions of each solution were administered to five groups of 5 mice each.

TABLE 3

| Test compound | Route of administration | $ED_{50}$, mg/kg |
|---|---|---|
| Example 5 | s.c. | 0.033 |
| Example 12 | s.c. | 0.028 |

TABLE 3-continued

| Test compound | Route of administration | ED$_{50}$, mg/kg |
|---|---|---|
| Cephaloridine | s.c. | 2.60 |

TABLE 4

| Test compound | Route of administration | ED$_{50}$, mg/kg |
|---|---|---|
| Example 15 | s.c. | 0.016 |
| Example 16 | s.c. | 0.035 |
| Cephaloridine | s.c. | 1.81 |

EXAMPLE 1

Production of 7-(4-bromo-2-hydroxyimino-3-oxobutyrylamino)-3-methyl-3-cephem-4-carboxylic acid (syn-isomer)

While a solution of 3.7 g of 7-(4-bromo-3-oxobutyrylamino)-3-methyl-3-cephem-4-carboxylic acid in 37 ml of acetic acid was stirred under ice-cooling, a solution of 0.953 g of sodium nitrite in 4 ml of water was added dropwise over a period of one hour. Then, the mixture was further stirred at room temperature for 3 hours. The reaction mixture was shaken with 100 ml of a saturated aqueous solution of medium chloride and 200 ml of ethyl acetate, and the organic layer was taken, washed with a saturated aqueous solution of sodium chloride, dried and concentrated. To the residue was added ethyl ether and the mixture was stirred. The resultant powders were recovered by filtration. By the above procedure that were obtained 1.34 g of the captioned compound.

IR(KBr, cm$^{-1}$): 1770, 1695, 1660

NMR(100 MHz, d$_6$-DMSO, δ): 2.02(s, 3-CH$_3$), 3.46(ABq, J=19 Hz, 2-CH$_2$), 4.59(s, BrCH$_2$—), 5.08(d, J=5 Hz, 6-H), 5.69(dd, J=5 & 8Hz, 7-H), 9.22(d, J=8Hz, CONH), 13.07(s, =NOH)

Elemental analysis: Calcd. for C$_{12}$H$_{12}$BrN$_3$O$_6$S: C, 35.48; H, 2.98; N, 10.34 Found: C, 34.91; H, 3.25; N, 10.14

EXAMPLE 2

Production of sodium 7-[2-(2-imino-4-thiazolin-4-yl)-2-hydroxyiminoacetamido]-3-methyl-3-cephem-4-carboxylate (syn-isomer)

In 1.2 ml of dimethylacetamide was dissolved 0.122 g of 7-(4-bromo-2-hydroxyimino-3-oxobutyrylamino)-3-methyl-3-cephem-4-carboxylic acid (syn-isomer) together with 0.03 g of thiourea and the mixed solution was stirred at room temperature for 1.5 hours. The reaction mixture was stirred with 10 ml of ethyl ether and the supernatant fluid was discarded after being removed by decantation, followed by addition of 10 ml of ethyl ether. The above procedure was repeated twice. The resultant powders were collected by filtration and dissolved in 10 ml of 5% sodium carbonate. The solution was column-chromatographed on polystyrene resin (Amberlite XAD-2, Rohm & Haas Co.) and dextran gel (Sephadex LH-20, Pharmacia) in the order mentioned, development being carried out with water. The fractions containing the desired product were pooled and lyophilized. By the above procedure there was obtained 0.09 g of the captioned compound.

IR(KBr, cm$^{-1}$): 1760, 1590

NMR (100 MHz, d$_6$-DMSO+D$_2$O, δ): 1.93(s, 3-CH$_3$), 3.25(ABq, J=18Hz, 2-CH$_2$), 4.96 (d, J=5Hz, 6-H), 5.57(d, J=5Hz, 7-H), 6.71(s, thiazoline 5-H)

Elemental analysis: Calcd. for C$_{13}$H$_{12}$N$_5$O$_5$S$_2$Na·3H$_2$O: C, 33.99; H, 3.95; N, 15.24; Found: C, 34.24; H, 4.15; N, 15.13

EXAMPLE 3

Production of 7-(4-chloro-2-hydroxyimino-3-oxobutyrylamino)-3-acetoxymethyl-3-cephem-4-carboxylic acid (syn-isomer)

While a mixture of 22.4 g (57.4 mM) of 7-(4-chloro-3-oxobutyrylamino)-3-acetoxymethyl-3-cephem-4-carboxylic acid and 200 ml of acetic acid was stirred under ice-cooling, a solution of 5.5 g (79.7 mM) of sodium nitrite in 20 ml of water was added dropwise over a quarter of an hour. The ice bath was removed and after the mixture had reached room temperature, it was stirred for 3.5 hours. To the reaction mixture were added 600 ml of a saturated aqueous solution of sodium chloride and the mixture was extracted 4 times with 250 ml portions of ethyl acetate. The extracts were combined, washed with water, dried and concentrated under reduced pressure. The above procedure yielded 14.31 g of crystals of the captioned compound.

IR(KBr, cm$^{-1}$): 1790

NMR(100 MHz, d$_6$-DMSO, δ): 2.05(s, CH$_3$CO), 3.43 & 3.66(ABq, J=18Hz, 2-CH$_2$), 4.70 & 5.02(ABq, J=13Hz, 3-CH$_2$), 4.08(s, ClCH$_2$), 5.15(d, J=5Hz, 6-H), 5.79(dd, J=5 & 8Hz, 7-H), 9.28 (d, J=8Hz, CONH), 13.17(s, =N—OH).

Elemental analysis: Calcd. for C$_{14}$H$_{14}$ClN$_3$O$_8$S·H$_2$O: C, 38.41; H, 3.68; N, 9.60; Found: C, 38.53; H, 3.31; N, 9.32

EXAMPLE 4

Production of 7-[2-(2-imino-4-thiazolin-4-yl)-2-hydroxyiminoacetamido]-3-acetoxymethyl-3-cephem-4-carboxylic acid hydrochloride (syn-isomer)

In 50 ml of dimethylacetamide there were dissolved 10.4 g (24.9 mM) of 7-(4-chloro-2-hydroxyimino-3-oxobutyrylamino)-3-acetoxymethyl-3-cephem-4-carboxylic acid (syn-isomer) together with 1.89 g of thiourea and the solution was stirred at room temperature for 3.5 hours. The solvent was distilled off under reduced pressure and the residue was stirred with ethyl ether. The supernatant fluid was discarded after being removed by decantation. Ethyl acetate was added to the residue and the supernatant fluid was discarded. Then, such admixing of the residue with ethyl ether and with ethyl acetate was carried out in turn four times. The resultant powders were recovered by suction-filtration and dried. By the above procedure the captioned compound was obtained.

IR(KBr, cm$^{-1}$): 1781

NMR (100 MHz, d$_6$-DMSO, δ): 2.04(s, CH$_3$CO), 3.45 & 3.68 (ABq, J=18Hz, 2-CH$_2$), 4.72 & 5.02(ABq, J=13Hz, 3-CH$_2$), 5.19(d, J=5Hz, 6-H), 5.79(dd, J=5 & 8Hz, 7-H), 6.88(s, thiazoline 5-H), 8.8(br. s, H$_2$N$^+$= & thiazoline NH), 9.64(d, J=8Hz, CONH), 12.41(br, s, =N—OH)

EXAMPLE 5

Production of sodium
7-[2-(2-imino-4-thiazolin-4-yl)-2-hydroxyimino-
acetamido]-3-acetoxymethyl-3-cephem-4-carboxylate
(syn-isomer)

In 1 ml of dimethylacetamide was dissolved 0.209 g of 7-(4-chloro-2-hydroxyimino-3-oxobutyrylamino)-3-acetoxymethyl-3-cephem-4-carboxylic acid (syn-isomer) together with 0.038 g of thiourea and the mixed solution was stirred at room temperature for 2.5 hours. The reaction mixture was admixed with 10 ml of ethyl acetate, whereupon a gummy product separated. The supernatant fluid was discarded after being removed by decantation and the residue was mixed with 10 ml of ethyl ether. The resultant powders were collected by filtration, immediately dissolved in a solution of 0.084 g of sodium hydrogen carbonate in 10 ml of water and chromatographed on a column of dextran gel (Sephadex LH-20, Pharmacia), development being carried out with water. The fractions containing the desired product were pooled and lyophilized. By the above procedure there was obtained 0.098 g of the captioned compound.

IR (KBr, cm$^{-1}$): 1765

NMR (100 MHz, d$_6$-DMSO, δ): 2.02(s, CH$_3$CO), 3.21 & 3.51(ABq, J=18Hz, 2-CH$_2$), 4.82 & 5.04(ABq, J=13Hz, 3-CH$_2$), 5.04(d, J=5Hz, 6-H), 5.66 (dd, J=5 & 8Hz, 7-H), 6.64(s, thiazoline 5-H), 7.11 (br. s, HN= & thiazoline NH), 9.35(d, J=8Hz, CONH), 12.0(br. =N—OH)

NMR(100 MHz, D$_2$O, δ): 2.14(s, CH$_3$CO), 3.39 & 3.71(ABq, J=18Hz, 2-CH$_2$), 4.74 & 4.94(ABq, J=13Hz, 3-CH$_2$), 5.25(d, J=5Hz, 6-H), 5.86 (d, J=5Hz, 7-H), 6.99(s, thiazoline 5-H)

Elemental analysis: Calcd. for C$_{15}$H$_{14}$N$_5$O$_7$S$_2$Na·2H$_2$O: C, 36.07; H, 3.63; N, 14.02; Found: C, 35.78; H, 3.57; N, 14.13

EXAMPLE 6

Production of sodium
7-[2-(2-imino-4-thiazolin-4-yl)-2-hydroxyimino-
acetamido]-3-acetoxymethyl-3-cephem-4- carboxylate
(syn-isomer)

In a solution of 0.2 g sodium hydrogen carbonate in 4 ml of water was dissolved of 0.619 g of 7-[2-(2-imino-4-thiazolin-4-yl)-2-hydroxyimino-acetamido]-3-acetoxymethyl-3-cephem-4-carboxylic acid hydrochloride. The solution was subjected to column chromatography on dextran gel (Sephadex LH-20, Pharmacia), development being carried out with water. The fractions containing the desired product were pooled and lyophilized. By the above procedure there was obtained 0.42 g of the captioned compound.

IR and NMR spectra of this compound were in good agreement with those of the product obtained in Example 5.

EXAMPLE 7

Production of
7-[2-(2-imino-4-thiazolin-4-yl)-2-hydroxyimino-
acetamido]-3-acetoxymethyl-3-cephem-4-carboxylic
acid (syn-isomer)

To a mixture of 0.309 g of 7-[2-(2-imino-4-thiazolin-4-yl)-2-hydroxyimino-acetamido]-3-acetoxymethyl-3-cephem-4-carboxylic acid hydrochloride (syn-isomer) and 1 ml of acetic acid there was added a sufficient amount of 1N-hydrochloric acid to completely dissolve the former. This solution was subjected to column chromatography on polystyrene resin (Amberlite XAD-2, Rohm & Haas Co.), development being carried out with water and 20% ethanol in the order mentioned. The fractions containing the desired product were pooled, concentrated and lyophilized. By the above procedure the captioned compound was obtained.

IR(KBr,cm$^{-1}$): 1770

NMR(100 MHz, d$_6$-DMSO, δ): 2.04(s, CH$_3$CO), 3.38 & 3.62(ABq, J=18Hz, 2-CH$_2$), 4.72 & 5.00(ABq, J=13Hz, 3-CH$_2$), 5.13(d, J=5Hz, 6-H), 5.78(dd, J=5 & 8Hz, 7-H), 6.67(s, thiazoline 5-H), 7.04(br. s, HN=& thiazoline NH), 9.37(d, J=8Hz, CONH), Elemental analysis: Calcd. for C$_{15}$H$_{15}$N$_5$O$_7$S$_2$·1.5H$_2$O: C, 38.46; H, 3.87; N, 14.95; Found: C, 38.59; H, 3.81; N, 14.93

EXAMPLE 8

Production of
7-(4-bromo-2-hydroxyimino-3-oxobutyrylamino)-3-
acetoxymethyl-3-cephem-4-carboxylic acid
(syn-isomer)

While a mixture of 4.5 g of 7-(4-bromo-3-oxobutyrylamino)-3-acetoxymethyl-3-cephem-4-carboxylic acid and 10 ml of acetic acid was stirred under ice-cooling, 0.76 g of sodium nitrite was added. The ice-bath was removed and the mixture was stirred at room temperature for one hour. The acetic acid was distilled off under reduced pressure, and 200 ml of ethyl acetate and 100 ml of water were added to the residue. The mixture was adjusted to pH 2 with a sufficient amount of phosphoric acid and shaken intensively. The organic layer was taken, washed with water, dried and concentrated to dryness. The residue was stirred with a small amount of ethyl acetate and the resultant powders were collected by filtration. By the above procedure there were obtained 2.0 g of the captioned compound.

IR(KBr, cm$^{-1}$); 1790, 1710, 1655, 1550

NMR (100 MHz, d$_6$-DMSO, δ): 2.05(s, CH$_3$CO), 3.44 & 3.67(ABq, J=18Hz, 2-CH$_2$), 4.59(s, BrCH$_2$—), 4.70 & 5.02(ABq, J=13Hz, 3-CH$_2$), 5.14(d, J=4.5Hz, 6-H), 5.79(dd, J=4.5 & 8.0Hz, 7-H), 9.28(d, J=8Hz, CONH), 13.10(s, =N—OH).

Elemental analysis: Calcd. for C$_{14}$H$_{14}$BrN$_3$O$_8$S: C, 36.22; H, 3.04; N, 8.82, Found: C, 37.36; H, 3.14; N, 8.82

EXAMPLE 9

Production of sodium
7-[2-(2-imino-4-thiazolin-4-yl)-2-hydroxyimino-
acetamido]-3-acetoxymethyl-3-cephem-4-carboxylate
(syn-isomer)

In 1 ml of dimethylacetamide was dissolved 0.232 g of 7-(4-bromo-2-hydroxyimino-3-oxobutyrylamino)-3-acetoxymethyl-3-cephem-4-carboxylic acid (syn-isomer) together with 0.038 g of thiourea and the mixed solution was stirred at room temperature for 2.5 hours. The reaction mixture was admixed with 10 ml of ethyl acetate, whereupon a gummy product separated out. The supernatant fluid was removed by decantation and the residue was admixed with 10 ml of ethyl ether. The resultant powders were collected by filtration and immediately dissolved in a solution of 0.084 g sodium hydrogen carbonate in 10 ml water. The solution was subjected to column chromatography on dextran gel (Sephadex LH-20, Pharmacia), development being carried out with water. The fractions containing the desired product were pooled and lyophilized. By the above procedure there was obtained 0.112 g of the captioned compound.

IR and NMR spectra of this product were in good agreement with those of the product obtained in Example 5.

EXAMPLE 10

Production of 7-(4-chloro-2-hydroxyimino-3-oxobutyrylamino)-3-(mandelyloxymethyl)-3-cephem-4-carboxylic acid (syn-isomer)

While solution of 0.47 g (1 mM) of 7-(4-chloro-3-oxobutyrylamino)-3-(mandelyloxymethyl)-3-cephem-4-carboxylic acid in 2 ml of acetic acid was stirred under ice-cooling a solution of 0.1 g (1.5 mM) of sodium nitrite in 0.2 ml of water was added dropwise over a period of one hour. The mixture was then stirred at room temperature for one hour. The acetic acid was distilled off under reduced pressure and 50 ml of ethyl acetate and 30 ml of water were added to the residue. The mixture was shaken vigorously and the organic layer was taken, washed with a saturated aqueous solution of sodium chloride and dried. The solvent was then evaporated off and, with the addition of 30 ml ether and 30 ml petroleum ether to the residue, the vessel wall was scratched. By this procedure there was obtained 0.29 g of the captioned compound as powders.

IR(KBr, cm$^{-1}$): 1780, 1741, 1715(sh.), 1675(sh.), 1640(sh.), 1540

NMR(100 MHz, d$_6$-DMSO, δ): 3.24(br, s, 2-CH$_2$), 4.77 & 5.07(ABq, J=13Hz, 3-CH$_2$), 5.04(d, J=5Hz, 6-H), 5.18(s,

5.79(dd, J=5 & 8Hz, 7-H), 7.3–7.5(m, C$_6$H$_5$—), 9.26(d, J=8Hz, —CONH—), 13.10(s, =N—OH).

EXAMPLE 11

Production of 7-[2-(2-imino-4-thiazolin-4-yl)-2-hydroxyimino-acetamido]-3-(mandelyloxymethyl)-3-cephem-4-carboxylic acid hydrochloride (syn-isomer)

In 2 ml of dimethylacetamide there was dissolved 0.24 g (0.5 mM) of 7-(4-chloro-2-hydroxyimino-3-oxobutyrylamino)-3-(mandelyloxymethyl)-3-cephem-4-carboxylic acid (syn-isomer) together with 0.042 g (0.55 mM) of thiourea and the mixed solution was stirred at room temperature for 2 hours. The solvent was distilled off under reduced pressure and 60 ml of ethyl acetate were added to the residue, followed by stirring. The resultant powders were collected by filtration, washed with ether and dried. By the above procedure there was obtained 0.26 g of the captioned compound as powders.

IR(KBr, cm$^{-1}$): 1776, 1741, 1672, 1631, 1536

NMR (100 MHz, d$_6$-DMSO, δ): 3.26(br. s, 2-CH$_2$), 4.78 & 5.08(ABq, J=13Hz, 3-CH$_2$), 5.08(d, J=5Hz, 6-H), 5.18(s,

5.78(dd, J=5 & 8Hz, 7-H), 6.86(s, thiazoline 5-H), 7.3–7.5(m, C$_6$H$_5$—), 9.61(d, J=8Hz, CONH).

EXAMPLE 12

Production of sodium 7-[2-(2-imino-4-thiazolin-4-yl)-2-hydroxyimino-acetamido]-3-(1-methyl-1H-tetrazol-5-yl)-thiomethyl-3-cephem-4-carboxylate (syn-isomer)

In 20 ml of phosphate buffer (0.2 M, pH 6.4) there was dissolved 0.883 g of 7-[2-(2-imino-4-thiazolin-4-yl)-2-hydroxyimino-acetamido]-3-acetoxymethyl-3-cephem-4-carboxylic acid hydrochloride together with 0.232 g of 1-methyl-1H-tetrazole-5-thiol and 0.336 g of sodium hydrogen carbonate and the mixed solution was stirred at 70° C. for 3 hours. The reaction mixture was subjected to column chromatography on polystyrene resin (Amberlite XAD-2, Rohm and Haas Co.), development being carried out with water. The fractions containing the desired product were pooled and lyophilized. By the above procedure there was obtained 0.217 g of the captioned compound.

IR(KBr, cm$^{-1}$): 1763

NMR (100MHz, d$_6$-DMSO, δ): 3.41 & 3.66(ABq, J=18Hz, 2-CH$_2$), 3.93(s, tetrazole-CH$_3$), 4.28 & 4.46(ABq, J=13Hz, 3-CH$_2$), 5.04(d, J=5 Hz, 6-H), 5.77(dd, J=5 & 8Hz, 7-H), 6.64(s, thiazoline 5-H), 7.12(br. s, HN= & thiazoline NH), 9.38(d, J=8Hz, CONH), 11.84(br. s, =NOH).

NMR(100 MHz, D$_2$O, δ): 3.47 & 3.82(ABq, J=18Hz, 2-CH$_2$), 4.05(s, tetrazole-CH$_3$), 4.08 & 4.34(ABq, J=13Hz, 3-CH$_2$), 5.22(d, J=5Hz, 6-H), 5.80(d, J=5Hz, 7-H), 6.98(s, thiazoline 5-H).

Elemental analysis: Calcd. for C$_{15}$H$_{14}$N$_9$O$_5$S$_3$Na·H$_2$O: C, 33.52; H, 3.00; N, 23.45; Found: C, 33.40; H, 3.47; N, 21.66

EXAMPLE 13

Production of sodium 7-[2-(2-imino-4-thiazolin-4-yl)-2-hydroxyimino-acetamido]-3-(1,2,3-triazol-5-yl)thiomethyl-3-cephem-4-carboxylate (syn-isomer)

In 20 ml of phosphate buffer (0.2 M, pH 6.4) there was dissolved 0.883 g of 7-[2-(2-imino-4-thiazolin-4-yl)-2-hydroxyimino-acetamido]-3-acetoxymethyl-3-cephem-4-carboxylic acid hydrochloride (syn-isomer) together with 0.202 g of 1,2,3-triazole-5-thiol and 0.336 g of sodium hydrogen carbonate and the mixed solution was stirred at a temperature of 70° C. for 1.5 hours. The reaction mixture was subjected to column chromatography on polystyrene resin (Amberlite XAD-2, Rohm and Haas Co.), development being carried out with water. The fractions containing the desired product were pooled and lyophilized. By the above procedure there was obtained 0.128 g of the captioned compound.

IR(KBr, cm$^{-1}$): 1765

NMR(100 MHz d$_6$-DMSO, δ): 3.39 & 3.58(ABq, J=18Hz, 2-CH$_2$), 3.95 & 4.30(ABq, J=13Hz, 3-CH$_2$), 5.02 (d, J=5Hz, 6-H), 6.66(s, triazoline 5-H), 7.19(br. s, HN= & thiazoline NH), 7.66(triazole 4-H)

Elemental analysis: Calcd. for C$_{15}$H$_{13}$N$_8$O$_5$S$_3$Na·1·5H$_2$O: C, 33.90; H, 3.03; N, 21.08; Found: C, 33.91; H, 3.68; N, 19.27

EXAMPLE 14

Production of sodium 7-[2-(2-imino-4-thiazoline-4-yl)-2-hydroxyimino-acetamido]-3-(3-methyl-1,2,4-thiadiazol-5-yl)thiomethyl-3-cephem-4-carboxylate (syn-isomer)

In 20 ml of phosphate buffer (0.2 M, pH 6.4) there was dissolved 0.663 g of 7-[2-(2-imino-4-thiazolin-4-yl)-2-hydroxyimino-acetamido]-3-acetoxymethyl-3-cephem-4-carboxylic acid hydrochloride (syn-isomer) together with 0.198 g of 3-methyl-1,2,4-thiadiazole-5-thiol and 0.252 g of sodium hydrogen carbonate and the mixture was stirred at a temperature of 70° C. for 3.5 hours. The reaction mixture was subjected to column chromatography on polystyrene resin (Amberlite XAD-2, Rohm and Haas Co.), development being carried out with water and 20% ethanol in the order mentioned. The fractions containing the desired product were pooled and lyophilized. By the above procedure there was obtained 0.142 g of the captioned compound.

IR(KBr, cm$^{-1}$): 1767

NMR (100 MHz, d$_6$-DMSO, δ): 2.52(s, thiadiazole-CH$_3$), 3.35 & 3.64(ABq, J=18Hz, 2-CH$_2$), 4.44 & 4.58(ABq, J=13Hz, 3-CH$_2$), 5.05(d, J=5Hz, 6-H, 5.66(dd, J=5 & 8Hz, 7-H), 6.64(s, thiazoline 5-H), 7.11(br. s, HN= & thiazoline NH), 9.46(d, J=8Hz, CONH)

Elemental analysis: Calcd. for C$_{16}$H$_{14}$N$_7$O$_5$S$_4$Na·3H$_2$O: C, 32.59; H, 3.42; N, 16.63; Found: C, 32.59; H, 3.29; N, 16.08

EXAMPLE 15

Production of sodium 7-[2-(2-imino-4-thiazolin-4-yl)-2-hydroxyimino-acetamido]-3-(4-methyl-1,2,4-triazol-3-yl)thiomethyl-3-cephem-4-carboxylate (syn-isomer)

In 20 ml of phosphate buffer (0.2 M, pH 6.4) there was dissolved 0.883 g of 7-[2-(2-imino-4-thiazolin-4-yl)-2-hydroxyimino-acetamido]-3-acetoxymethyl-3-cephem-4-carboxylic acid hydrochloride (syn-isomer) together with 0.23 g of 4-methyl-1,2,4-triazole-3-thiol and 0.336 g of sodium hydrogen carbonate and the mixed solution was stirred at a temperature of 70° C. for 3.5 hours. The reaction mixture was subjected to column chromatography on polystyrene resin (Amberlite XAD-2, Rohm and Haas Co.), development being carried out with water. The fractions containing the desiredproduct were pooled and lyophilized. By the above procedure there was obtained 0.371 g of the captioned compound.

IR(KBr, cm$^{-1}$): 1770

NMR (100 MHz, d$_6$-DMSO, δ): 3.59(s, triazole-CH$_3$), 3.38 & 3.62(ABq, J=18Hz, 2-CH$_2$), 4.18 & 4.30(AB q, J=13Hz, 3-CH$_2$), 4.99(d, J=5Hz, 6-H), 5.64(dd, J=5 & 8Hz, 7-H), 6.64(s, thiazoline; 5-H, 7.12(br. s, HN= & thiazoline NH), 8.48(s, triazole 5-H), 9.43(d, J=8Hz, CONH), 12.0(br. =NOH).

Elemental analysis: Calcd. for C$_{16}$H$_{15}$N$_6$O$_5$S$_3$Na·2.5-H$_2$O: C, 34.10; H, 3.58; N, 19.88; Found: C, 34.11; H, 3.72; N, 19.54

EXAMPLE 16

Production of sodium 7-[2-(2-imino-4-thiazolin-4-yl)-2-hydroxyimino-acetamido]-3-(2-methyl-1,3,4-thiadiazol-5-yl)thiomethyl-3-cephem-4-carboxylate (syn-isomer)

In 10 ml of water there was dissolved 0.53 g (0.93 mM) of 7-[2-(2-imino-4-thiazolin-4-yl)2-hydroxyimino-acetamido]-3-(mandelyloxymethyl)-3-cephem-4-carboxylic acid hydrochloride (syn-isomer) together with 0.2 g (1.5 mM) of 2-methyl-1,3,4-thiazol-5-thiol and 0.28 g (3.4 mM) of sodium hydrogen carbonate and the mixed solution was stirred at 60° C. for 50 minutes. The reaction mixture was subjected to column chromatography on polystyrene resin (Amberlite XAD-2, Rohm and Haas Co.), development being carrid out with water and 10% ethanol in the order mentioned. The fractions containing the desired product were pooled, concentrated and lyophilized. The resultant powders were dissolved in 2 ml of water and the solution was chromatographed on a column of dextran gel (Sephadex LH-20, Pharmacia), water being used as the developing solvent. The fractions containing the desired product were pooled and lyophilized. By the above procedure there was obtained 0.19 g of the captioned compound.

IR(KBr, cm$^{-1}$): 1767, 1666, 1600, 1542

NMR (100 MHz, d$_6$-DMSO, δ): 2.68(s, thiadiazole-CH$_3$), 3.36 & 3.63 (ABq, J=18Hz, 2-CH$_2$), 4.35 & 4.56(ABq, J=13Hz, 3-CH$_2$), 5.04(d, J=5Hz, 6-H), 5.66(dd, J=5 & 8Hz, 7-H), 6.64(s, thiazoline 5-H), 7.10(br. s, HN= & thiazoline NH), 9.35(d, J=8Hz, CONH), 11.92(br. s, =NOH)

NMR(100 MHz, D$_2$O, δ): 2.73(s, thiadiazole-CH$_3$), 3.43 & 3.81(ABq, J=18Hz, 2-CH$_2$), 4.03 & 4.49(ABq, J=13Hz, 3-CH$_2$), 5.22(d, J=5Hz, 6-H), 5.83(d, J=5Hz, 7-H), 6.99(s, thiazoline 5-H)

Elemental analysis: Calcd. for C$_{16}$H$_{14}$N$_7$O$_5$S$_4$Na·2H$_2$O: C, 33.62; H, 3.17; N, 17.15; Found: C, 33.88; H, 3.20; N, 16.86

EXAMPLE 17

Production of 7-[2-(2-imino-4-thiazolin-4-yl)-2-hydroxyimino-acetamido]-3-(4-carbamoylpyridiniummethyl)-3-cephem-4-carboxylate (syn-isomer)

A mixture of 0.883 g of 7-[2-(2-imino-4-thiazolin-4-yl)-2-hydroxyimino-acetamido]-3-acetoxymethyl-3-cephem-4-carboxylic acid hydrochloride (syn-isomer), 0.492 g isonicotinamide, 2 g of potassium iodide, 0.168 g of sodium hydrogen carbonate and 0.2 M-phosphate buffer (pH 6.4) was stirred at a temperature of 70° C. for 3.5 hours. The reaction mixture was subjected to column chromatography on polystyrene resin (Amberlite XAD-2, Rohm and Haas Co.) and, then, on dextran gel (Sephadex LH-20, Pharmacia) in the order mentioned, water being used as the developing solvent. The fractions containing the desired product were pooled and lyophilized. By the above procedure there was obtained 0.041 g of the captioned compound.

IR(KBr, cm$^{-1}$): 1773

NMR(100 MHz, d$_6$-DMSO, δ): 3.10 & 3.57(ABq, J=18Hz, 2-CH$_2$), 5.08(d, J=5Hz, 6-H), 5.23 & 5.75(ABq, J=14Hz, 3-CH$_2$), 5.69(dd, J=5 & 8Hz, 7-H), 6.62(s, thiazoline 5-H), 7.05(br. s, HN= & thiazoline NH), 8.17 & 8.74 (each br. s, CONH$_2$), 8.45 & 9.55(ABq, J=6Hz, pyridinium ring protons), 9.32(d, J=8Hz, CONH)

Elemental analysis: Calcd. for C$_{19}$H$_{17}$N$_7$O$_6$S$_2$·4H$_2$O: C, 39.65; H, 4.38; N, 17.04; Found: C, 39.28; H, 3.91; N, 16.97

EXAMPLE 18

Production of sodium 7-[2-(2-imino-4-thiazolin-4-yl)-2-hydroxyimino-acetamido]-3-hydroxymethyl-3-cephem-4-carboxylate (syn-isomer)

In 5 ml of water there was dissolved 0.57 g of 7-[2-(2-imino-4-thiazolin-4-yl)-2-hydroxyimino-acetamido]-3-(mandelyloxymethyl)-3-cephem-4-carboxylic acid hydrochloride (syn-isomer) together with 0.17 g of sodium hydrogen carbonate and, while the mixed solution was stirred under ice-cooling, 0.55 ml of 2N-sodium hydroxide was added. The mixture was stirred at that temperature for 3 hours and, then, at room temperature for 1 hour. The reaction mixture was subjected to column chromatography on polystyrene resin (Amberlite XAD-2, Rohm and Haas Co.), development being carried out with water. The fractions containing the desired product were pooled and lyophilized. By the above procedure there was obtained 0.19 g of the captioned compound.

IR(KBr, $cm^{-1}$): 1766, 1622(sh.), 1604, 1530

NMR (100 MHz, $D_2O$, δ): 3.46 & 3.72(ABq, J=18Hz, 2-$CH_2$), 4.31(s, 3-$CH_2$), 5.25(d, J=5Hz, 6-H), 5.84(d, J=5Hz, 7-H), 7.01(s, thiazoline 5-H)

Elemental analysis: Calcd. for $C_{13}H_{12}N_5O_6S_2Na \cdot 2H_2O$: C, 34.14; H, 3.53; N, 15.31; Found: C, 34.23; H, 3.52; N, 15.17

EXAMPLE 19

Production of 7-(4-chloro-2-hydroxyimino-3-oxobutyrylamino)-3-(1-methyl-1H-tetrazol-5-yl)thiomethyl-3-cephem-4-carboxylic acid (syn-isomer)

While a mixture of 22.3 g of 7-(4-chloro-3-oxobutyrylamino)-3-(1-methyl-1H-tetrazol-5-yl) thiomethyl-3-cephem-4-carboxylic acid and 200 ml of acetic acid was stirred under ice-cooling, a solution of 3.8 g of sodium nitrite in 20 ml of water was added dropwise over a period of 15 minutes. The cooling bath was removed and the mixture was stirred at room temperature for 3 hours. The reaction mixture was diluted with 600 ml of a saturated aqueous solution of sodium chloride and extracted 4 times with 250 ml portions of ethyl acetate. The extracts were pooled, washed with water, dried and concentrated to dryness under reduced pressure. The residue was stirred with 200 ml of ethyl ether and the resultant powders were collected by filtration. By the above procedure there was obtained 19.0 g of the captioned compound.

IR(KBr, $cm^{-1}$): 1785

NMR (100 MHz, $d_6$-DMSO, δ): 3.57 & 3.79(ABq, J=18Hz, 2-$CH_2$), 3.94(s, tetrazole-$CH_3$), 4.20 & 4.37(ABq, J=13Hz, 3-$CH_2$), 4.73(s, $ClCH_2$), 5.13(d, J=5 Hz, 6-H), 5.78(dd, J=5 & 8 Hz, 7-H), 9.28(d, J=8 Hz, CONH)

Example 20

Production of sodium 7-[2-(2-imino-4-thiazolin-4-yl)-2-hydroxyimino-acetamido]-3-(1-methyl-1H-tetrazol-5-yl)thiomethyl-3-cephem-4-carboxylate (syn-isomer)

In 1 ml of dimethylacetamide there was dissolved 0.238 g of 7-(4-chloro-2-hydroxyimino-3-oxobutyrylamino)-3-(1-methyl-1H-tetrazol-5-yl)thiomethyl-3-cephem-4-carboxylic acid (syn-isomer) together with 0.038 g of thiourea and the mixed solution was stirred at room temperature for 2.5 hours. The reaction mixture was admixed with 10 ml of ethyl acetate, whereupon a gummy substance separated. The supernatant fluid was removed by decantation and the residue was admixed with 10 ml of ethyl ether. The resultant powders were collected by filtration, immediately dissolved in a solution of 0.084 g of sodium hydrogen carbonate in 10 ml of water and chromatographed on a column of dextran gel (Sephadex LH-20, Pharmacia) using water as the developing solvent. The fractions containing the desired product were pooled and lyophilized. By the above procedure there was obtained 0.112 g of the captioned compound.

IR and NMR spectra of this product were in good agreement with those of the product obtained in Example 12.

EXAMPLE 21

Production of 7-(4-bromo-2-hydroxyimino-3-oxobutyrylamino)-3-(1-methyl-1H-tetrazol-5-yl)thiomethyl-3-cephem-4-carboxylic acid (syn-isomer)

While a mixture of 3.43 g of 7-(4-bromo-3-oxobutyrylamino)-3-(1-methyl-1H-tetrazol-5-yl)thiomethyl-3-cephem-4-carboxylic acid and 24 ml of acetic acid was stirred under cooling with ice, a solution of 0.532 g of sodium nitrite in 2.5 ml of water was added dropwise. The mixture was stirred for 10 minutes and then for one more hour at room temperature after the ice bath was removed, and the mixture was shaken vigorously with 60 ml of a saturated solution of water and 100 ml of ethyl acetate. The organic layer was taken, washed with a saturated aqueous solution of sodium chloride, dried and concentrated under reduced pressure. The residue was stirred with 100 ml of ethyl ether and the resultant powders were recovered. By the above procedure there were obtained 2.763 g of the captioned compound.

IR(KBr, $cm^{-1}$): 1780

NMR(100 MHz, $d_6$-DMSO, δ): 3.57 & 3.79(ABq, J=18 Hz, 2-$CH_2$), 3.96(s, tetrazole-$CH_3$), 4.23 & 4.39(ABq, J=14 Hz, 3-$CH_2$), 4.79(s, $BrCH_2$—), 5.12(d, J=5 Hz, 6-H), 5.76(dd, J=5 & 8 Hz, 7-H), 9.27(d, J=8 Hz, CONH)

EXAMPLE 22

Production of 7-[2-(2-imino-4-thiazolin-4-yl)-2-hydroxyimino-acetamido]-3-(1-methyl-1H-tetrazol-5-yl)thiomethyl-3-cephem-4-carboxylic acid hydrobromide (syn-isomer)

In 4 ml of dimethylacetamide there were dissolved 1.04 g of 7-(4-bromo-2-hydroxyimino-3-oxobutyrylamino)-3-(1-methyl-1H-tetrazol-5-yl)thiomethyl-3-cephem-4-carboxylic acid (syn-isomer) together with 0.152 g of thiourea and the mixture was stirred at room temperature for 90 minutes. To the above reaction mixture were added 50 ml of ethyl ether and, after stirring, the supernatant fluid was discarded after being removed by decantation. To the residue ethyl ether was added and the same procedure was repeated. This cycle was repeated a few times and the resultant powders were recovered by suction-filtration and dried. By the above procedure there were obtained 1.058 g of the captioned compound.

IR(KBr, $cm^{-1}$): 1781

NMR (100 MHz, $d_6$-DMSO, δ): 3.58 & 3.80(ABq, J=18 Hz, 2-$CH_2$); 3.95(s, tetrazole —$CH_3$), 4.23 & 4.40 (ABq, J=14 Hz, 3-$CH_2$), 5.15 (d, J=5 Hz, 6-H), 5.75(dd, J=5 & 8 Hz, 7-H), 6.83(s, thiazoline 5-H), 9.58(d, J=8 Hz, CONH), 12.20 (broad s, =N—OH)

EXAMPLE 23

Production of sodium
7-[2-(2-imino-4-thiazolin-4-yl)-2-hydroxyimino-acetamido]-3-(1-methyl-1H-tetrazol-5-yl)thiomethyl-3-cephem-4-carboxylate (syn-isomer)

In a solution of 0.168 g of sodium hydrogen carbonate in 4 ml of water was dissolved 0.578 g of 7-[2-(2-imino-4-thiazolin-4-yl)-2-hydroxyimino-acetamido]-3-(1-methyl-1H-tetrazol-5-yl)thiomethyl-3-cephem-4-carboxylic acid hydrobromide. The solution was subjected to column chromatography on dextran gel (Sephadex LH-20, Pharmacia), development being carried out with water. The fractions including the desired product were pooled and lyophilized. By the above procedure there was obtained 0.267 g of the captioned compound.

IR and NMR spectra of this product were in agreement with those of the product obtained in Example 12.

EXAMPLE 24

Production of
7-[2-(imino-4-thiazolin-4-yl)-2-hydroxyimino-acetamido]-3-nitrogen-containing heterocyclic thiomethyl-3-cephem-4-carboxylic acid [I],
-hydrochloride, -betaine or -sodium salt (syn-isomer)

One of the following production processes 1 to 4 was selected to produce the compounds listed in Table 5. The physical properties of the compounds are shown in the same table.

General Production Process 1

In 40 ml of phosphate buffer (0.1 M, pH 6.4) there was dissolved 0.956 g (2 mM) of 7-[2-(2-imino-4-thiazolin-4-yl)-2-hydroxyimino-acetamido]-3-acetoxymethyl-3-cephem-4-carboxylic acid hydrochloride (syn-isomer) together with 2.2 mM of a nitrogen-containing heterocyclic thiol and 0.504 g (6 mM) of sodium hydrogen carbonate and the solution was stirred at a temperature of 60°–65° C. for 7 to 8 hours. The reaction mixture was concentrated under reduced pressure to about 20 ml and, after adjustment to pH 6.5 with 10% sodium hydrogen carbonate or 10% phosphoric acid if necessary, the concentrate was subjected to column chromatography on polystyrene resin (Amberlite XAD-2, Rohm and Haas Co.), development being carried out with water, 5% ethanol and 10% ethanol in the order mentioned. The fractions containing the desired product were pooled and the alcohol was distilled off under reduced pressure. Finally the residue was lyophilized. By the above procedure there was obtained the captioned compound, i.e. 7-[2-(2-imino-4-thiazolin-4-yl)-2-hydroxyimino-acetamido]-3-nitrogen-containing heterocyclic thiomethyl-3-cephem-4-carboxylic acid, -hydrochloride, -betaine or -sodium (syn-isomer).

General Production Process 2

In 20 ml of water there were dissolved 1.14 g (2 mM) of 7-[2-(2-imino-4-thiazolin-4-yl)-2-hydroxyimino-acetamido]-3-(mandelyloxymethyl)-3-cephem-4-carboxylic acid hydrochloride (syn-isomer) together with 2.2 mM of a nitrogen-containing heterocyclic thiol and 0.52 g (6.2 mM) of sodium hydrogen carbonate, and the mixed solution was stirred at a temperature of 60° C. for 50 minutes. After adjustment to pH 6.5 with 10% sodium carbonate or 10% phosphoric acid if necessary, the above solution was subjected to column chromatography on polystyrene resin (Amberlite XAD-2, Rohm and Haas Co.), development being carried out with water, 5% ethanol and 10% ethanol in the order mentioned. The fractions containing the desired product were pooled and the alcohol was distilled off under reduced pressure. The residue was lyophilized. By the above procedure there was obtained the indicated compound, i.e. 7-[2-(2-imino-4-thiazolin-4-yl)-2-hydroxyimino-acetamido]-3-nitrogen-containing heterycyclic thiomethyl-3-cephem-4-carboxylic acid, -hydrochloride, -betaine or -sodium (syn-isomer).

General Production Process 3

(1) In 40 ml of water there were dissolved 10.7 g (30 mM) of 7-acetoacetamido-3-acetoxymethyl-3-cephem-4-carboxylic acid together with 5.04 g (60 mM) of sodium hydrogen carbonate and 30 mM of a nitrogen-containing heterocyclic thiol. After adjustment to pH 7.0 with 10% sodium hydroxide, the above solution was stirred at a temperature of 60°–65° C. for 4 hours. After cooling, 2.31 g (33 mM) of hydroxylamine hydrochloride was added. Then, the pH were adjusted to 3.6 with a sufficient amount of 1N-hydrochloric acid. The solution was allowed to stand at room temperature overnight. The resultant crystals were collected by filtration, washed with acetone and dried. Where the object compound was water-soluble and did not precipitate out, the reaction mixture was adjusted to pH 3.3 and concentrated under reduced pressure to about 50 ml. To the residue there were added 1500 ml of ethanol and the mixture was stirred under ice-cooling for 4 hours. The resultant crystals were collected by filtration, washed with ethanol and dried. By the above procedure there was obtained a 7-amino-3-nitrogen-containing heterocyclic thiomethyl-3-cephem-4-carboxylic acid.

(2) While a solution of 1.03 g (13 mM) of diketene in 5 ml of methylene chloride was cooled at −30° C., 15 g of a solution of 1 mol (by wt.) chlorine in carbon tetrachloride (15 mM) or a solution of 2.24 g (14 mM) of bromine in 5 ml of methylenechloride were added dropwise. Separately, a 7-amino-3-nitrogen-containing heterocyclic thiomethyl-3-cephem-4-carboxylic acid (10 mM) and 2.02 g (20 mM) of triethylamine were dissolved in 20 ml of methylene chloride and cooled to −20° C. Then, the above reaction mixture was quickly added dropwise to this cooled solution. In many instances, heat was evolved to bring the mixture to about 0° C. The liquid temperature was increased gradually to room temperature, at which the mixture was stirred for 15 minutes. To the reaction mixture were added 150 ml of ethyl acetate together with 100 ml of 10% phosphoric acid and the mixture was vigorously stirred. The organic layer was separated, washed with water, dried and concentrated. The residue was loosened with ether. By the above procedure there were obtained powders of 7-[4-chloro(where chlorine was used) or bromo (where bromine was used)-3-oxobutyrylamino]-3-nitrogen-containing heterocyclic thiomethyl-3-cephem-4-carboxylic acid.

(3) While a mixture of 7 mM of a 7-(4-chloro- or bromo-3-oxobutyrylamino)-3-nitrogen-containing heterocyclic thiomethyl-3-cephem-4-carboxylic acid and 24 ml of acetic acid was stirred under ice-cooling, a solution of 0.532 g (7.7 mM) of sodium nitrite in 2.5 ml of water was added dropwise. This mixture was stirred for 10 minutes and, after the ice-bath was removed, was stirred at room temperature for one hour. To this reaction mixture there were added 60 ml of a saturated aqueous solution of sodium chloride together with 100 ml of ethyl acetate and the mixture was shaken vigorously. The organic layer was taken, dried and concentrated to dryness. The residue was loosened with ethyl ether and the resultant powders were collected by filtration and dried. By the above procedure there was obtained a 7-(4-chloro- or bromo-2-hydroxyimino-3-oxobutyrylamino)-3-nitrogen-containing heterocyclic thiomethyl-3-cephem-4-carboxylic acid (syn-isomer).

(4) In 4 ml of dimethylacetamide there were dissolved 2 mM of a 7-(4-chloro- or bromo-2-hydroxyimino-3-oxobutyrylamino)-3-nitrogen-containing heterocyclic thiomethyl-3-cephem-4-carboxylic acid (syn-isomer) together with 0.152 g (2 mM) of thiourea and the mixed solution was stirred at room temperature for 90 minutes. To this mixed solution there were added 50 ml of ethyl ether and, after stirring, the supernatant fluid was discarded by decantation. Then, ethyl ether was added to the residue and the mixture was treated in the like manner. The above procedure was repeated a few times and the resultant powders were collected by filtration. The powders were dissolved in 20 ml of water and, after adjustment to pH 6.5, the solution was subjected to column chromatography using polystyrene resin (Amberlite XAD-2, Rohm and Haas Co.), development being carried out with water and 10% ethanol in the order mentioned. The fractions containing the desired product were collected, concentrated and lyophilized. By the above procedure there was obtained the indicated 7-[2-(2-imino-4-thiazolin-4-yl)-2-hydroxyimino-acetamido]-3-nitrogen-containing heterocyclic thiomethyl-3-cephem-4-carboxylic acid betaine or sodium (syn-isomer).

General Production Process 4

(1) In 300 ml of water there were dissolved 31.4 g (0.1 mol) of 7-amino-3-(3-oxobutyryloxy)methyl-3-cephem-4-carboxylic acid, 18.5 g (0.22 mol) of sodium hydrogen carbonate and 0.1 mol of a nitrogen-containing heterocyclic thiol and, after adjustment to pH 5.5, the mixed solution was heated at 60° C. for one hour. After cooling, the reaction mixture was washed once with dichloromethane and the water layer was adjusted to pH 3.3 and stirred under ice-cooling for one hour. The precipitate was recovered by filtration, washed with water, methanol and acetone in the order mentioned and dried. By the above procedure there was obtained a 7-amino-3-nitrogen-containing heterocyclic thiomethyl-3-cephem-4-carboxylic acid. Where the object compound was water-soluble and did not precipitate out, the reaction mixture was adjusted to pH 3.3 and concentrated under reduced pressure to about 50 ml. To the residue there were added 1500 ml of ethanol and the mixture was stirred under ice-cooling for 4 hours. The resultant crystals were collected by filtration, washed with ethanol and dried. By the above procedure there was obtained a 7-amino-3-nitrogen-containing heterocyclic thiomethyl-3-cephem-4-carboxylic acid.

(2) Using the 7-amino-3-nitrogen-containing heterocyclic thiomethyl-3-cephem-4-carboxylic acid obtained above, the procedures of General Production Process 3-(2), (3) and (4) were followed to obtain the desired 7-[2-(2-imino-4-thiazolin-4-yl)-2-hydroxyimino-acetamido]-3-nitrogen-containing heterocyclic thiomethyl-3-cephem-4-carboxylic acid, betaine or sodium (syn-isomer).

TABLE 5

| Compound No. | R | M | IR β-lactam (KBr, cm$^{-1}$) | NMR δppm | Process |
|---|---|---|---|---|---|
| 1 | ![N——N / S triazole-like] | Na | 1763 | (100MHz,D$_2$O):3.40 & 3.79(ABq, J=18Hz,2-CH$_2$),4.10 & 4.52 (ABq, J=13Hz,3-CH$_2$), 5.19(d,J=5Hz,6-H), 5.80(d,J=5Hz,7-H), 6.99(s,thiazoline 5-H) | 1 2 3 4 |
| 2 | ![N——N / O, CH$_3$] | Na | 1763 | (100MHz,D$_2$O):2.55(s, oxadiazole-CH$_3$),3.41 & 3.84(ABq,J=18Hz,2-CH$_2$), 3.98 & 4.49(ABq,J=13Hz, 3-CH$_2$),5.21(d,J=5Hz, 6-H),5.82(d,J=5Hz,7-H), 6.98(s,thiazoline 5-H) | 1 2 3 4 |
| 3 | ![N——N / N-H] | Na | 1766 | (100MHz,D$_2$O):3.44 & 3.79(ABq,J=18Hz,2-CH$_2$), 4.04 & 4.25(ABq,J=13Hz, 3-CH$_2$), 5.21(d,J=5Hz, 6-H), 5.82(d,J=5Hz,7-H), 6.99(s,thiazoline 5-H), 8.36(s,triazole 5-H) | 1 2 3 4 |

TABLE 5-continued

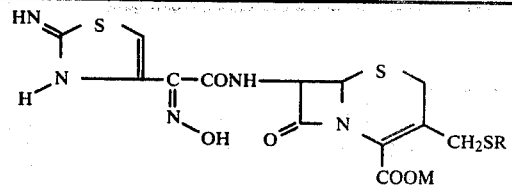

| Compound No. | R | M | IR β-lactam (KBr, cm$^{-1}$) | NMR δppm | Process |
|---|---|---|---|---|---|
| 4 | (triazole with N-CH₃ and CH₃ substituents) | Na | 1763 | (100MHz,D₂O):2.51(s, triazole 3-CH₃),3.42 & 3.96(ABq,J=18Hz,2-CH₂), 3.68(s,triazole 4-CH₃), 3.75 & 4.38(ABq,J=14Hz, 3-CH₂),5.23(d,J=4Hz, 6-H),5.83(d,J=4Hz,7-H), 6.99(s,thiazoline 5-H) | 1 2 3 4 |
| 5 | (imidazole with N-CH₃) | Na | 1760 | (100MHz,D₂O):3.31 & 3.86(ABq,J=18Hz,2-CH₂), 3.64 & 4.32(ABq,J=13Hz, 3-CH₂), 3.78(s, imidazole 1-CH₃), 5.22 (d,J=5Hz,6-H),5.82 (d,J=5Hz,7-H),6.99 (s,thiazoline 5-H),7.14 & 7.30(each d,J=1Hz, imidazole 4-& 5-H) | 1 2 3 4 |
| 6 | (thiadiazole with CF₃) | Na | 1763 | (100MHz,D₂O):3.55 & 3.88(ABq,J=18Hz,2-CH₂), 4.31 & 4.67(ABq,J=13Hz, 3-CH₂),5.30(d,J=5Hz, 6-H),5.92(d,J=5Hz,7-H), 6.99(s,thiazoline 5-H) | 1 2 4 |
| 7 | (thiazole with 4-CH₃ and 5-CH₃) | Na | 1760 | (100MHz,D₂O):2.34 & 2.76(each s, thiazole 4- & 5-CH₃), 3.40 & 3.82(ABq,J=18Hz,2-CH₂), 3.90 & 4.49(ABq,J=13 Hz, 3-CH₂),5.25(d,J=5Hz, 6-H),5.90(d,J=5Hz,7-H), 6.98(s,thiazoline 5-H) | 1 2 4 |
| 8 | (thiazole with CH₃) | Na | 1760 | (100MHz,D₂O):2.55(s, thiazole 5-CH₃),3.41 & 3.87(ABq,J=18Hz,2-CH₂), 3.91 & 4.59(ABq,J=14Hz, 3-CH₂),5.26(d,J=5Hz, 6-H),5.88(d,J=5Hz,7-H), 6.98(s,thiazoline 5-H), 7.51(s,thiazole 4-H) | 4 |
| 9 | (thiazole with CH₃) | H | 1760 | (100MHz,d₆DMSO):2.32 (s,thiazole 4-CH₃),3.46 & 3.73(ABq,J=18Hz,2-CH₂), 4.11 & 4.49(ABq,J=13Hz, 3-CH₂), 5.20(d,J=5Hz, 6-H), 5.75(dd, J=5 & 8Hz,7-H),6.23(s,thiazole 5-H), 6.67(s,thiazoline 5-H), 7.1(br.s,=NH & thiazoline NH), 9.38 (d,J=8Hz,CONH) | 1 2 3 4 |
| 10 | (tetrazole with N-Na and CH₃) | Na | 1758 | (100MHz,D₂O):3.41 & 3.78(ABq,J=18Hz,2-CH₂), 3.99 & 4.32 (ABq,J=13Hz, 3-CH₂),5.25(d,J=5Hz,6-H), 5.87(d,J=5Hz,7-H),6.98 s,thiazoline 5-H) | 1 2 4 |
| 11 | (thiazole with NH₂) | Na | 1760 | (100MHz,D₂O):3.43 & 3.86(ABq,J=18Hz,2-CH₂), 3.90 & 4.48(ABq,J=13Hz, 3-CH₂), 5.30(d,J=5Hz, 6-H), 5.90(d,J=5Hz,7-H), 6.99(s,thiazoline 5-H) | 1 2 |

TABLE 5-continued

Structure: cephalosporin with 2-(2-iminothiazolin-4-yl)-2-(hydroxyimino)acetamido side chain and 3-CH$_2$SR substituent, COOM at 4-position.

| Compound No. | R | M | IR β-lactam (KBr, cm$^{-1}$) | NMR δppm | Process |
|---|---|---|---|---|---|
| 12 | (1,3,4-thiadiazol-2-yl, 5-NHCOOCH$_3$) | Na | 1760 | (100MHz,D$_2$O): 3.46 & 3.90(ABq,J=18Hx,2-CH$_2$), 3.90(s,OCH$_3$), 3.92 & 4.49(ABq,J=13Hz,3-CH$_2$), 5.30(d,J=5Hz,6-H), 5.90(d,J=5Hz,7-H), 6.99(s, thiazoline 5-H) | 1, 2, 3, 4 |
| 13 | (1,3,4-thiadiazol-2-yl, 5-CH$_2$CON(CH$_3$)$_2$) | Na | 1758 | (100NHz,D$_2$O):3.12 & 3.29(each, N(CH$_3$)$_2$), 3.53 & 3.87(ABq,J=18Hz, 2-CH$_2$), 4.19 & 4.58(ABq, J=14Hz,3-CH$_2$), 5.33(d, J=5Hz,6-H), 5.93(d,J=5Hz 7-H), 6.99(s,thiazoline 5-H) | 1, 2, 3, 4 |
| 14 | (1,3,4-thiadiazol-2-yl, 5-CH$_2$COONa) | Na | 1761 | (100MHz,D$_2$O):3.55 & 3.94(ABq,J=18Hz,2-CH$_2$), 4.16(s,CH$_2$CO), 4.19 & 4.60(ABq,J=13Hz,3-CH$_2$), 5.35(d,J=5Hz,6-H), 5.94(d,J=5Hz,7-H), 6.99(s, thiazoline 5-H) | 1, 2, 4 |
| 15 | (1,3,4-thiadiazol-2-yl, 5-CH$_2$COOCH$_3$) | Na | 1760 | (100MHz,D$_2$O):3.51 & 3.89(ABq,J=18Hz,2-CH$_2$), 3.91(s,OCH$_3$), 4.19 & 4.56(ABq,J=13Hz,3-CH$_2$), 5.31(d,J=5Hz,6-H), 5.90(d,J=5Hz,7-H), 6.99 (s,thiazoline 5-H) | 1, 2, 3, 4 |
| 16 | (1,3,4-thiadiazol-2-yl, 5-CH$_2$CONH$_2$) | Na | 1762 | (100MHz,D$_2$O):3.50 & 3.88(ABq,J=18Hz,2-CH$_2$), 4.19 & 4.55 (ABq, J=13Hz, 3-CH$_2$), 5.30(d,J=5Hz, 6-H),5.90(d,J=5Hz,7-H), 6.98(s,thiazoline 5-H) | 1, 2, 3, 4 |
| 17 | (1,3,4-thiadiazol-2-yl, 5-CH$_2$SCH$_3$) | Na | 1762 | (100NHz,D$_2$O):2.24(s, CH$_3$S), 3.52 & 3.87(ABq, J=18Hz,2-CH$_2$), 4.21(s, CH$_2$S), 4.26 & 4.57(ABq, J=14Hz,3-CH$_2$), 5.31(d, J=5Hz,6-H), 5.93(d,J= 5Hz,7-H), 6.99(s, thiazoline 5-H) | 1, 2, 3, 4 |
| 18 | (1,3,4-thiadiazol-2-yl, 5-CH$_2$OCH$_3$) | Na | 1763 | (100MHz,D$_2$O):3.36(s, OCH$_3$), 3.28 & 3.84(ABq, J=18Hz,2-CH$_2$), 3.98 & 4.36(ABq,J=14Hz,3-CH$_2$), 4.76(s,CH$_2$O),5.07(d, J=5Hz, 6-H), 5.67(d, J=5Hz,7-H), 6.99(s, thiazoline 5-H) | 1, 2, 3, 4 |
| 19 | (1,3,4-thiadiazol-2-yl, 5-SCH$_2$COONa) | Na | 1763 | (60MHz,D$_2$O):3.35 & 3.74 (ABq,J=16Hz,2-CH$_2$), 3.97 & 4.38(ABq,J=14Hz,3-CH$_2$), 5.19(d,J=5Hz,6-H), 5.78 (d,J=5Hz,7-H), 6.98(s, thiazoline 5-H) | 1, 2, 3, 4 |
| 20 | (1,3,4-thiadiazol-2-yl, 5-SCH$_2$CH$_2$OH) | Na | 1765 | (60MHz,D$_2$O):3.4–3.8(m, 2 × CH$_2$), 3.95(t,J=6Hz, CH$_2$O), 4.01 & 4.38(ABq, J=14Hz,3-CH$_2$), 5.16(d, J=5Hz,6-H), 5.77(d,J= 5Hz,7-H), 6.99(s, thiazoline 5-H) | 1, 2, 3, 4 |

TABLE 5-continued (Structure shown: guanidinyl-thiazoline connected via C=N-OH and C-CONH to β-lactam with CH₂SR and COOM groups)

| Compound No. | R | M | IR β-lactam (KBr, cm$^{-1}$) | NMR δppm | Process |
|---|---|---|---|---|---|
| 21 | (N=N thiadiazole with CH₃ at one position, S bridge, CH₂NHC(=NH)NH₂) | H | 1765 | (100MHz,CF₃COOH):3.79 (s,2-CH₂), 4.45 & 4.84 (ABq,J=14Hz,3-CH₂), 5.14(d,J=7Hz,CH₂NH), 5.36(d,J=5Hz, 6-H) 5.99(dd, J=5 & 8Hz,7-H), 6.4–6.9(br.,guanyl 4 × H), 6.99(s, thiazoline 5-H) | 2, 4 |
| 22 | (thiadiazole-CH₃, CH₂OH) | Na | 1765 | (100MHz,D₂O):3.43 & 3.81(ABq,J=18Hz,2-CH₂), 4.07 & 4.56(ABq,J=13Hz 3-CH₂), 4.96(s,CH₂O), 5.23(d,J=5Hz,6-H), 5.84(d,J=5Hz,7-H), 6.99 (s,thiazoline 5-H) | 1, 2, 4 |
| 23 | (thiadiazole-CH₃, CH₂N(CH₃)₂) | Na | 1762 | (100MHz,D₂O):2.51(s, N(CH₃)₂, 3.43 & 3.80 (ABq,J=18Hz,2-CH₂), 4.11 & 4.50(ABq,J=13Hz,3-CH₂), 4.21(s,thiadiazole-CH₂N), 5.21(d,J=5Hz,6-H), 5.82(d,J=5Hz,7-H), 6.98(s,thiazoline 5-H) | 1, 2, 4 |
| 24 | (thiadiazole-CH₃, SCH₂CH₂SO₃Na) | Na | 1763 | (60MHz,D₂O):3.1–3.8 (m,6 × H), 4.02 & 4.25(ABq,J=13Hz,3-CH₂), 5.14(d,J=5Hz,6-H), 5.73 (d,J=5Hz,7-H), 6.99(s, thiazoline 5-H) | 1, 2, 4 |
| 25 | (thiadiazole-CH₃, CH₂CH₂OH) | Na | 1760 | (100MHz,D₂O): 2.93(t, J=6Hz, thiadiazole-CH₂), 3.3–4.0(× H), 4.08 & 4.56(ABq,J=14Hz,3-CH₂), 5.23(d,J=5Hz,6-H), 5.84 (d,J=5Hz,7-H), 6.99(s, thiazoline 5-H) | 1, 2, 3, 4 |
| 26 | (thiadiazole-CH₃, CH₂CH₂N(CH₃)₂) | Na | 1768 | (100MHz,D₂O): 3.02 (S,N(CH₃)₂), 3.45 & 3.82(ABq,J=18Hz,2-CH₂), 3.67(br.s,CH₂CH₂), 4.07 & 4.52(ABq,J=13Hz,3-CH₂), 5.27(d,J=5Hz,6-H), 5.84 (d,J=5Hz,7-H), 6.99(s, thiazoline 5-H) | 2, 3, 4 |
| 27 | (triazole N-CH₃, CH₂OH) | Na | 1760 | (100MHz,D₂O): 3.39 & 3.83(ABq,J=18Hz,2-CH₂), 3.74(s,CH₃), 3.71 & 4.31(ABq,J=13Hz,3-CH₂), 4.82(s,CH₂O), 5.17(d,J=5Hz,6-H), 5.79(d,J=5Hz, 7-H), 6.99(s,thiazoline 5-H) | 1, 2, 4 |
| 28 | (triazole N-CH₃, CH₂OAc) | Na | 1760 | (100MHz,D₂O): 2.24(s, CH₃CO), 3.41 & 3.72(ABq, J=18Hz,2-CH₂), 3.76(s, triazole -CH₃), 3.85 & 4.30(ABq,J=13Hz,3-CH₂), 5.28(d,J=5Hz,6-H), 5.36 (s,CH₂O), 5.83(d,J=5Hz, 7-H), 6.99(s,thiazoline 5-H) | 1, 2, 4 |

TABLE 5-continued

Structure: compound with HN-C(=S)-NH-... -C(=N-OH)-CONH-[β-lactam]-CH₂SR with COOM

| Compound No. | R | M | IR β-lactam (KBr, cm⁻¹) | NMR δppm | Process |
|---|---|---|---|---|---|
| 29 | tetrazole-N-(CH₂)₂N(CH₃)₂ (⊕) with CH₃ at C | ⊖ | 1768 | (100MHz,D₂O): 3.01(s, N(CH₃)₂), 3.47 & 3.79 (ABq,J=18Hz,2-CH₂), 3.78(t,J=6Hz,CH₂NMe₂), 4.10 & 4.25(ABq,J=13Hz, 3-CH₂), 5.20(d,J=5Hz,6-H), 5.76(d,J=5Hz,7-H), 6.99 (s,thiazoline 5-H) | 1 2 4 |
| 30 | tetrazole-N-(CH₂)₃N(CH₃)₂ with CH₃ at C | Na | 1760 | (100MHz,D₂O): 2.4(m, C—CH₂—C), 2.95(s,N (CH₃)₂),3.3(m, CH₂NMe₂), 3.45 & 3.81(ABq, J=18Hz, 2-CH₂), 4.12 & 4.33(ABq, J=13Hz,3-CH₂), 4.42(t, J=7Hz,tetrazole-CH₂—C), 5.20(d,J=5Hz,6-H), 5.80 (d,J=5Hz,7-H), 6.98(s, thiazoline 5-H) | 1 2 4 |
| 31 | tetrazole-N-(CH₂)₂NHCH₃ · HCl with CH₃ at C | H | 1770 | (100MHz,D₂O): 2.96(s, NCH₃), 3.62 & 3.95(ABq, J=18Hz,2-CH₂), 3.83 & 4.94(each t, J=6Hz, CH₂CH₂), 5.33(d,J-4.5Hz, 6-H), 5.87(d,J=4.5Hz, 7-H), 6.99(s,thiazoline 5-H) | 2 |
| 32 | tetrazole-N-CH₂CH₂NHCOCH₃ with CH₃ at C | Na | 1765 | (100MHz,D₂O): 2.02(s, CH₃CO), 3.51 & 3.83(ABq, J=18Hz,2-CH₂), 3.73(t, J=6Hz,CH₂NAc), 4.21 & 4.41(ABq, J=13Hz,3-CH₂), 4.61(t,J=6Hz, tetrazole-CH₂—C), 5.28(d, J=5Hz,6-H), 5.85(d,J=5Hz, 7-H), 6.98(s,thiazoline 5-H) | 1 2 4 |
| 33 | tetrazole-N-(CH₂)₂NH₃ (⊕) with CH₃ at C | ⊖ | 1765 | (100MHz,D₂O + NaHCO₃): 3.44 & 3.76 (ABq, J= 18Hz,2-CH₂), 3.46–3.8(m, tetrazole-C—CH₂N), 4.0–5.0(m, 3-CH₂ & tetrazole-CH₂), 5.20(d, J=4.5Hz, 6-H), 5.77(d, J=4.5Hz,7-H), 6.98(s, thiazoline 5-H) | 2 |
| 34 | tetrazole-N-CH₂OCH₃ with CH₃ at C | Na | 1770 | (100MHz,D₂O): 3.45(s, OCH₃), 3.45 & 3.81(ABq, J=18Hz,2-CH₂), 4.17 & 4.42(ABq,J=13Hz,3-CH₂), 5.21(d,J=4.5Hz,6-H), 5.77(s,tetrazole-CH₂O), 5.81(d,J=4.5Hz,7-H), 6.98(s,thiazoline 5-H) | 1 2 4 |
| 35 | tetrazole-N-CH₂SCH₃ with CH₃ at C | Na | 1765 | (100MHz,D₂O): 2.22(s, SCH₃), 3.44 & 3.79(ABq, J=18Hz,2-CH₂), 4.21 & 4.42(ABq,J=13Hz,3-CH₂), 5.22(d,J=5Hz,6-H), 5.47(s,tetrazole-CH₂S), 5.81(d,J=5Hz,7-H), 6.98 (s,thiazoline 5-H) | 1 2 4 |

TABLE 5-continued

Structure shown at top of table: cephalosporin with aminothiazole oxime side chain and CH₂SR at 3-position.

| Compound No. | R | M | IR β-lactam (KBr, cm$^{-1}$) | NMR δppm | Process |
|---|---|---|---|---|---|
| 36 | 5-methyl-1-(CH₂)₂OH-tetrazol-1-yl (via N) | Na | 1760 | (100MHz,D₂O): 3.42 & 3.78(ABq,J=18Hz,2-CH₂), 4.03(t,J=6Hz,CH₂O), 4.12 & 4.36(ABq,J=13Hz, 3-CH₂), 4.55(t,J=6Hz, tetrazole —CH₂—C), 5.19 (d,J=5Hz,6-H), 5.78(d, J=5Hz,7-H), 6.98(s, thiazoline 5-H) | 1, 2, 4 |
| 37 | 5-methyl-1-CH₂CONH₂-tetrazolyl | Na | 1765 | (100MHz,D₂O): 3.51 & 3.85(ABq,J=18Hz,2-CH₂), 4.23 & 4.46(ABq,J=13Hz, 3-CH₂), 5.29(d,J=5Hz, 6-H), 5.42(s,tetrazole —CH₂CO), 5.89(d,J=5Hz, 7-H), 6.99(s, thiazoline 5-H) | 1, 2, 4 |
| 38 | 5-methyl-1-CH₂COONa-tetrazolyl | Na | 1761 | (100MHz,d₆-DMSO + D₂O): 3.42 & 3.68(ABq,J=18Hz 2-CH₂), 4.21 & 4.37(ABq, J=13Hz,3-CH₂), 4.70 (s,tetrazole —CH₂CO), 5.07(d,J=5Hz,6-H), 5.73(d,J=5Hz,7-H), 6.99(s,thiazoline 5-M) | 1, 2, 4 |
| 39 | 5-methyl-1-methyl-3-CH₂COONa-1,2,4-triazolyl | Na | 1760 | (100MHz,D₂O): 3.41 & 3.72(ABq, J=18Hz,2-CH₂), 3.60(s,triazole —CH₃), 3.78(s,triazole —CH₂CO₂), 3.85 & 4.30 (ABq, J=13Hz, 3-CH₂), 5.17(d,J=5Hz,6-H) 5.79(d,J=5Hz,7-H), 6.99(s,thiazoline 5-H) | 1, 2, 4 |
| 40 | 5-methyl-2-CH₂CH₃-thiadiazolyl | Na | 1765 | (100MHz,D₂O): 1.37(t, J=7Hz,CH₃), 3.08(q, J=7Hz,CH₂CH₃), 3.50 & 3.62(ABq, J=18Hz,2-CH₂), 4.03 & 4.34(ABq, J=13Hz, 3-CH₂), 5.18(d,J=5Hz, 6-H), 5.80(d,J=5Hz,7-H), 6.99(s,thiazoline 5-H) | 1, 2, 3 |
| 41 | 5-methyl-1-methyl-3-NH₂-1,2,4-triazolyl | Na | 1760 | (100MHz,D₂O): 3.44 & 3.97(ABq, J=18Hz,2-CH₂), 3.57(s,triazole —CH₃) 3.67 & 4.33(ABq, J=13Hz, 3-CH₂), 5.26(d,J=5Hz,6-H), 5.85(d,J=5Hz, 7-H), 6.98(s,thiazoline 5-H) | 1, 2 |
| 42 | 5-methyl-1-CH₂CH₂COONa-tetrazolyl | Na | 1765 | (100MHz,D₂O): 2.88(t, J=7Hz,CH₂CO₂), 3.51 & 3,83(ABq, J=18Hz,2-CH₂), 4.14 & 4.38(ABq, J=13Hz,3-CH₂), 4.61(t, J=7Hz,tetrazole —CH₂C), 5.23(d,J=5Hz, 6-H), 5.84(d,J=5Hz, 7-H), 6.99(s, thiazoline 5-H | 1, 2, 4 |

TABLE 5-continued

Structure:

HN=C(NH)-S-CH=C(-C(=NOH)-CONH-[β-lactam]-CH₂SR with COOM

| Compound No. | R | M | IR β-lactam (KBr, cm⁻¹) | NMR δppm | Process |
|---|---|---|---|---|---|
| 43 | [thiazole]-CH₂COONa (N=C-S-CH= with CH₂COONa) | Na | 1763 | (100MHz, D₂O): 3.43 & 3.84(ABq, J=18Hz, 2-CH₂) 3.76(s, CH₂CO), 3.98 & 4.54(ABq, J=14Hz, 3-CH₂) 5.24(d, J=5Hz, 6-H), 5.85 (d, J=5Hz, 7-H), 6.98 (s, thiazoline 5-H), 7.35(s, thiazole 5-H) | 2, 3, 4 |
| 44 | [thiadiazole]-NHCH₂CH₂OH | Na | 1765 | (60MHz, D₂O): 3.3–4.0 (m,3×CH₂), 4.33(ABq, 3-CH₂), 5.06(d, J=5Hz, 6-H), 5.68(d, J=5Hz, 7-H), 6.99 (s, thiazoline 5-H) | 2 |
| 45 | [thiadiazole]-NHCH₂CH₂N(CH₃)₂ | Na | 1760 | (60MHz, D₂O): 2.95(s, N(CH₃)₂), 3.56(m, 2×CH₂) 3.96(m, 2-CH₂), 4.34(m, 3-CH₂), 5.13(d, J=5Hz, 6-H), 5.70(d, J=5Hz, 7-H), 6.99(s, thiazoline 5-H) | 2 |
| 46 | [tetrazole]-CH₂CON(CH₃)₂ | Na | 1763 | (100MHz, D₂O): 3.03 & 3.21(each s, N(CH₃)₂), 3.42 & 3.76(ABq, J=18Hz, 2-CH₂), 4.15 & 4.37 (ABq, J=14Hz, 3-CH₂), 5.21(d, J=5Hz, 6-H), 5.30 & 5.53(each s, tetrazole —CH₂), 5.79 (d, J=5Hz, 7-H), 6.99 (s, thiazoline 5-H) | 2, 4 |
| 47 | [triazole N-CH₃]-CONH₂ | Na | 1765 | (60MHz, D₂O): 3.4–4.0 (m, 2-CH₂, triazole CH₃), 5.1–5.25(m, 6-H), 5.7–5.8(m, 7-H), 6.99 (s, thiazoline 5-H) | 2, 4 |

EXAMPLE 25

Production of 7-(4-bromo-2-hydroxyimino-3-oxobutyrylamino)-3-carbamoyloxymethyl-3-cephem-4-carboxylic acid (syn-isomer)

While a solution of 0.15 g of 7-(4-bromo-3-oxobutyrylamino)-3-carbamoyloxymethyl-3-cephem-4-carboxylic acid in 2 ml of acetic acid was stirred at room temperature, 0.03 g of sodium nitrite was added dropwise over a period of five minutes. Then, the mixture was further stirred for 20 minutes, after which time it was concentrated to dryness under reduced pressure. The resultant vitreous solid was applied to a Merck silica gel plate No. 5715 and developed with ethyl acetate-acetic acid-water (8:1:1). The color reaction with a 0.5% solution of copper chloride gave a single yellow spot at Rf=0.327. Therefore, the product was assumed to be substantially the captioned compound and was subjected to the next reaction.

EXAMPLE 26

Production of sodium 7-[2-(2-imino-4-thiazolin-4-yl)-2-hydroxyimino-acetamido]-3-carbamoyloxymethyl-3-cephem-4-carboxylate (syn-isomer)

In 1 ml of dimethylacetamide there was dissolved the crude 7-(4-bromo-2-hydroxyimino-3-oxobutyrylamino)-3-carbamoyloxymethyl-3-cephem-4-carboxylic acid (syn-isomer) prepared in Example 25, together with 0.03 g of thiourea. The mixed solution was stirred at room temperature for one hour. The reaction mixture was stirred with 50 ml of ethyl ether and the supernatant fluid was discarded after being removed by decantation. To the residue there were added 50 ml of ethyl ether and the mixture was treated as above. The resultant powders were collected by filtration and dissolved in 5 ml of a 5% aqueous solution of sodium hydrogen carbonate. The solution was subjected to column chromatography on polystyrene resin (Amberlite XAD-2, Rohm and Haas Co.), development being carried out with water. The fractions containing the desired product were pooled and lyophilized. By the above procedure there was obtained 0.063 g of the captioned compound.

IR(KBr, cm$^{-1}$): 3400, 1760, 1710, 1610, 1530, 1400, 1360, 1330 (carbamoyl C—N)

NMR(100 MHz, d$_6$-DMSO, δ): 4.72 & 4.86(ABq, J=12 Hz, 3-CH$_2$), 4.98(d, J=5 Hz,6-H), 5.63(dd, J=5 & 9 Hz, 7-H), 6.44(br. s, CONH$_2$), 6.72(s, thiazoline 5-H), 7.1(br., NH= & thiazoline —NH—)

EXAMPLE 27

Production of pivaloyloxymethyl 7-[2-(2-imino-4-thiazolin-4-yl)-2-hydroxyimino-acetamido]-3-(1-methyl-1H-tetrazol-5-yl)thiomethyl-3-cephem-4-carboxylate (syn-isomer)

10.9 g of sodium 7-[2-(2-imino-4-thiazolin-4-yl)-2-hydroxyimino-acetamido]-3-(1-methyl-1H-tetrazol-5-yl)thiomethyl-3-cephem-4-carboxylate (syn-isomer) were dissolved in 60 ml of dimethylformamide, and 4.9 g of iodomethyl pivalate dissolved in 5 ml of dimethylformamide were added dropwise to the solution under stirring and cooling with ice, the addition taking 10 minutes. Then, the mixture was further stirred for 10 minutes, and 700 ml of ethyl acetate were added. The resultant mixture was washed with water (150 ml×3) and dried over magnesium sulfate.

The dried solution was concentrated under reduced pressure, and 400 ml of diethyl ether were added to the residue, whereupon it became powdery. The powder was collected by filtration and dried under reduced pressure to obtain the above identified product. Yield 7.802 g IR(KBr, cm$^{-1}$): 1786

NMR(100 MHz, in d$_6$-DMSO,δ): 1.19(s,(CH$_3$)$_3$C), 3.62 and 3.82(ABq, J=18 Hz, 2-CH$_2$), 3.94(s, tetrazole-CH$_3$), 4.18 and 4.45 (ABq, J=14 Hz, 3-CH$_2$), 5.16(d, J=5 Hz, 6-H), 5.78 and 5.93ABq, J=6 Hz, OCH$_2$O-pivaloyl). near 5.8(m, 7-H), 6.67(s, thiazoline 5-H), 7.10(broad s, NH—C(=NH)—), 9.42 (d, J=8 Hz, CONH), 11.32(broad s, =NOH)

Elementary analysis: C$_{21}$H$_{25}$N$_9$O$_7$S$_3$.0.5H$_2$O: Calcd.: C, 40.64; H, 4.22; N, 20.31; Found: C, 40.72; H, 4.20; N, 19.46

EXAMPLE 28

Production of pivaloyloxymethyl 7-[2-(2-imino-4-thiazolin-4-yl)-2-hydroxyimino-acetamido]-3-(2-methyl-1,3,4-thiadiazol-5-yl)thiomethyl-3-cephem-4-carboxylate (syn-isomer)

0.143 g of sodium 7-[2-(2-imino-4-thiazolin-4-yl)-2-hydroxyimino-acetamido]-3-(2-methyl-1,3,4-thiadiazol-5-yl)thiomethyl-3-cephem-4-carboxylate (syn-isomer) was dissolved in 1 ml of dimethylformamide, and the solution was cooled with ice and stirred. To the solution there was added dropwise 0.071 g of iodomethyl pivalate dissolved in 1 ml of dimethylformamide. The resultant mixture was stirred for 10 minutes, followed by the addition of 5 ml of water and 50 ml of ethyl acetate. The mixture was vigorously agitated. The organic layer was separated, washed with water (10 ml × 3) and dried over magnesium sulfate. The dried solution was concentrated under reduced pressure to remove the solvents. 10 ml of diethyl ether were added to the residue to give a powder. The powder was collected by filtration and dried to obtain the above-identified product. Yield 0.07 g.

IR(KBr, cm$^{-1}$): 1782

NMR(100 MHz, in d$_6$-DMSO,δ): 1.19(s,(CH$_3$)$_3$C), 2.70(s, thiadiazol 2-CH$_3$), 3.61 & 3.83 (ABq, J=18 Hz, 2-CH$_2$), 4.17 & 4.57(ABq, J=14 Hz, 3-CH$_2$), 5.19(d, J=5 Hz, 6-H), 5.80 & 5.95 (ABq, J=6 Hz, OCH$_2$O-pivaloyl), near 5.8(m, 7-H), 6.69(s, thiazoline 5-H), 9.94(d, J=8 Hz, CONH), 11.41(broad s, =N—OH).

Elemental analysis: C$_{22}$H$_{25}$N$_7$O$_7$S$_4$.H$_2$O; Calcd.: C, 40.92; H, 4.21; N, 15.18; Found: C, 41.20; H, 4.25; N, 15.20

EXAMPLE 29

Production of pivaloyloxymethyl 7-[2-(2-imino-4-thiazolin-4-yl)-2-hydroxyimino-acetamido]-3-carbamoyloxymethyl-3-cephem-4-carboxylate (syn-isomer)

0.5 g of sodium 7-[2-(2-imino-4-thiazolin-4-yl)-2-hydroxyimino-acetamido]-3-carbamoyloxymethyl-3-cephem-4-carboxylate (syn-isomer) was dissolved in 3 ml of dimethylformamide to form a solution. 0.242 g of iodomethyl pivalate in 2 ml of dimethylformamide was added little by little to the above solution under stirring and cooling with ice. The reaction mixture was stirred for ten minutes, followed by the addition of 5 ml of water and 60 ml of ethyl acetate. The resultant mixture was vigorously agitated. The organic layer was separated, washed with water (10 ml × 3) and dried over sodium sulfate. The dried solution was concentrated under reduced pressure to remove the solvents, and 10 ml of diethyl ether were added to the residue to give a powder. The powder was collected by filtration and dried under reduced pressure to obtain the above identified product. Yield 0.327 g IR(KBr, cm$^{-1}$): 1795

NMR(100 MHz, in d$_6$-DMSO,δ); 1.18 (s, (CH$_3$)$_3$C), 3.46 and 3.66(ABq, J=18 Hz, 2-CH$_2$), 4.58 and 4.85(ABq, J=13 Hz, 3-CH$_2$), 5.19 (d, J=5 Hz, 6-H), 5.82(dd, J=5 & 8 Hz, 7-H), 5.79 and 5.92(ABq, J=6 Hz, OCH$_2$O-pivaloyl), 6.54(broad s, OCONH$_2$), 6.66 (s, thiazoline 5-H), 7.04(broad s, NH—C(=NH)—), 9.40 (d, J=8 Hz, CONH), 11.29(broad s, =NOH)

Elemental analysis: C$_{20}$H$_{24}$N$_6$O$_9$S$_2$.0.5H$_2$O: Calcd.: C, 42.47; H, 4.46; N, 14.86; Found: C, 42.79; H, 4.60; N, 14.47

EXAMPLE 30

Production of 1-(ethoxycarbonyloxy)ethyl 7-[2-(2-imino-4-thiazolin-4-yl)-2-hydroxyimino-acetamido]-3-carbamoyloxymethyl-3-cephem-4-carboxylate (syn-isomer)

1.0 g of sodium 7-[2-(2-imino-4-thiazolin-4-yl)-2-hydroxyimino-acetamido]-3-carbamoyloxymethyl-3-cephem-4-carboxylate (syn-isomer) was dissolved in 6 ml of dimethylformamide to form a solution. 1.37 g of 1-(ethoxycarbonyloxy)ethyl iodide were added to the solution, and the mixture was stirred for 5 days. To the mixture were added 150 ml of water and 200 ml of ethyl acetate, followed by vigorous stirring. The organic layer was separated, washed with water (100 ml × 2) and dried over magnesium sulfate. The dried solution was concentrated under reduced pressure, and 100 ml of petroleum ether were added to the residue to give a powder. The powder was collected by filtration to obtain the above identified product. Yield 0.07 g.

IR(KBr, cm$^{-1}$):1790

NMR(100 MHz, in d$_6$-DMSO,δ); 1.14(t, J=7 Hz, —CH$_2$CH$_3$), 1.51 (d, J=5 Hz, OCH(CH$_3$)O), 3.46 & 3.68(ABq, J=18 Hz, 2—CH$_2$), 4.18(q,J=7 Hz, —CH$_2$CH$_3$), 4.60 & 4.85(ABq, J=13 Hz, 3—CH$_2$), 5.10

(d, J=5 Hz, 6-H), 5.86(dd, J=5 & 8 Hz, 7-H), 6.55 (broad s, OCONH$_2$), 6.66(s, thiazoline 5-H), 6.74 (q, J=7 Hz, —CH(CH$_3$)—), 7.04(broad s, NH—(C=N-H)—), 9.38(d, J=8 Hz, CONH), 11.28(broad s, =NOH)

EXAMPLE 31

Production of 7-[2-(2-chloroacetylimino-4-thiazolin-4-yl)-2-acetoxyimino-acetamido]-3-acetoxymethyl-3-cephem-4-carboxylic acid (syn-isomer)

In 70 ml of methylene chloride there were suspended 2.14 g of 2-acetoxyimino-2-(2-chloroacetylimino-4-thiazolin-4-yl)acetic acid (syn-isomer), followed by the addition of 1.70 g of N,N-dimethylaniline. While the mixture was stirred at room temperature, 1.47 g of phosphorus pentachloride were added in small portions. The mixture was stirred for 1 hour. The methylene chloride was distilled off under reduced pressure and 21 ml of N,N-dimethylacetamide were added. Following the addition of 0.847 g of N,N-dimethylaniline, 1.90 g of 7-aminocephalosporanic acid were added. The mixture was stirred at room temperature for one hour. Upon addition of ether, a syrupy product separated out. The ether was discarded after being removed by decantation and the residue was dissolved by the addition of water and ethyl acetate. The ethyl acetate layer was washed with a saturated aqueous solution of sodium chloride and extracted with a 1% aqueous solution of sodium hydrogen carbonate. The aqueous alkali layer was adjusted to pH 2 with phosphoric acid and extracted with ethyl acetate. The ethyl acetate layer was washed with a saturated aqueous solution of sodium chloride and dried over magnesium sulfate. The solvent was distilled off under reduced pressure and, after addition of ether to the residue, the vessel wall was scratched, whereupon a powder was obtained. The powder was recovered by filtration and dried. By the above procedure there were obtained 1.770 g of 7-[2-(2-chloroacetylimino-4-thiazolin-4-yl)-2-acetoxyimino-acetamido]-3-acetoxymethyl-3-cephem-4-carboxylic acid (syn-isomer)

IR(cm$^{-1}$, KBr): 1784

NMR(100 MHz, d$_6$-DMSO, δ): 2.06(s, CH$_2$O-COCH$_3$), 2.22(s, =N—OCOCH$_3$), 3.49 & 3.71 (ABq, J=18 Hz, 2-CH$_2$), 4.39(s, ClCH$_2$), 4.72 & 5.03 (ABq, J=13 Hz, 3-CH$_2$), 5.23(d, J=5 Hz, 6-H), 5.89(dd, J=5 & 8 Hz, 7-H), 7.76(s, thiazoline 5-H), 9.93 (d, J=8 Hz, CONH), 12.96(br. s, thiazoline 3-H)

EXAMPLE 32

Production of 7-[2-(2-amidinothioacetylimino-4-thiazolin-4-yl)-2-acetoxyimino-acetamido]-3-acetoxymethyl-3-cephem-4-carboxylic acid hydrochloride (syn-isomer)

In 4 ml of N,N-dimethylacetamide there were dissolved 1.120 g of 7-[2-(2-chloroacetylimino-4-thiazolin-4-yl)-2-acetoxyimino-acetamido]-3-acetoxymethyl-3-cephem-4-carboxylic acid (syn-isomer), and under stirring at room temperature, 0.152 g of thiourea was added. The mixture was stirred at room temperature for 3.5 hours, after which time ether was added, whereupon an oily product separated. The ether was discarded after being removed by decantation and, after the addition of ethyl acetate to the residue, the vessel wall was scratched. The resultant powder was recovered by filtration, washed with ethyl acetate and dried. By the above procedure there were obtained 1.395 g of the captioned compound. This product contained a small amount of ethyl acetate and N,N-dimethylacetamide.

IR(KBr, cm$^{-1}$): 1779

NMR(100 MHz, d$_6$—DMSO, δ): 2.06(s, CH$_2$O-COCH$_3$), 2.22 (s, =N—OCOCH$_3$), 3.49 & 3.73(ABq, J=18 Hz, 2—CH$_2$), 4.41 (s, SCH$_2$CO), 4.72 & 5.03 (ABq, J=13 Hz, 3—CH$_2$), 5.23 (d, J=5 Hz, 6-H), 5.88(dd, J=5 & 8 Hz, 7-H), 7.76(s, thiazoline 5-H), 9.37(br. s,

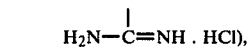

9.94(d, J=8 Hz, CONH), 13.00(br. s, thiazoline 3-H).

EXAMPLE 33

Production of sodium 7-[2-(2-imino-4-thiazolin-4-yl)-2-hydroxyimino-acetamido]-3-acetoxymethyl-3-cephem-4-carboxylate To a mixture of 10 ml of water and 10 ml of tetrahydrofuran there was added 0.350 g of 7-[2-(2-amidinothioacetylimino-4-thiazolin-4-yl)-2-acetoxyiminoacetamido]-3-acetoxymethyl-3-cephem-4-carboxylic acid hydrochloride (syn-isomer), followed by the addition of 139 mg of sodium hydrogen carbonate. The mixture was stirred at room temperature for 25 hours and, then, at 40° C. for 6 hours with stirring. The tetrahydrofuran was removed under reduced pressure and the resulting residue was subjected to column chromatography on polystyrene resin (Amberlite XAD-2, Rohm and Haas Co.), development being carried out with water. The fractions containing the desired product were pooled and lyophilized. By the above procedure there was obtained 0.116 g of the captioned compound. IR, NMR and elemental analysis of this product were in complete agreement with those of the compound obtained in Example 5.

EXAMPLE 34

Production of sodium 7-[2-(2-imino-4-thiazolin-4-yl)-2-hydroxyimino-acetamido]-3-acetoxymethyl-3-cephem-4-carboxylate (syn-isomer)

In a mixture of 10 ml of tetrahydrofuran and 10 ml of water there was dissolved 0.300 g of 7-[2-(2-chloroacetylimino-4-thiazolin-4-yl)-2-acetoxyimino-acetamido]-3-acetoxymethyl-3-cephem-4-carboxylic acid, followed by the addition of 0.136 g of sodium hydrogen carbonate and 0.053 g of thiourea. The mixture was stirred at room temperature for 24.5 hours and, then, at a temperature of 40° C. for 6.5 hours with stirring. The tetrahydrofuran was distilled off under reduced pressure and the resulting residue was subjected to column chromatography on polystyrene resin (Amberlite XAD-2, Rohm and Haas Co.), development being carried out with water. The fractions containing the desired product were pooled and lyophilized. By the above procedure there was obtained 0.09 g of the captioned compound. IR, NMR, elemental analysis and TLC of this product were in complete agreement with those of the compound obtained in Example 5.

EXAMPLE 35

Production of sodium 7-[2-(2-imino-4-thiazolin-4-yl)-2-hydroxyimino-acetamido]-3-acetoxymethyl-3-cephem-4-carboxylate (syn-isomer)

In 20 m of water there was suspended 0.525 g of 7-[2-(2-amidinothioacetylimino-4-thiazolin-4-yl)-2-acetoxyimino-acetamido]-3-acetoxymethyl-3-cephem-4-carboxylic acid hydrochloride (syn-isomer), followed by the addition of 0.252 g of sodium hydrogen carbonate. The mixture was stirred at room temperature for 15 hours. The reaction mixture, as such, was subjected to column chromatography on polystyrene resin (Amberlite XAD-2, Rohm and Haas Co.) and the fractions containing the desired product were pooled and lyophilized.

By the above procedure there was obtained 0.121 g of sodium 7-[2-(2-imino-4-thiazolin-4-yl)-2-hydroxyiminoacetamido]-3-acetoxymethyl-3-cephem-4-carboxylate (syn-isomer).

The former compound was in complete agreement with the product of Example 5 with respect to IR, NMR, elemental analysis and TLC.

EXAMPLE 36

Production of 7-[2-(2-chloroacetylimino-4-thiazolin-4-yl)-2-hydroxyimino-acetamido]-3-acetoxymethyl-3-cephem-4-carboxylic acid (syn-isomer)

In a mixture of 10 ml of tetrahydrofuran and 10 ml of water there was dissolved 0.350 g of 7-[2-(2-chloroacetylimino-4-thiazolin-4-yl)-2-acetoxyimino-acetamido]-3-acetoxymethyl-3-cephem-4-carboxylic acid (syn-isomer), followed by the addition of 0.105 g of sodium hydrogen carbonate. The mixture was stirred at room temperature for 13.5 hours, then at 40° C. for 20.5 hours and finally at 50° C. for 10 hours. The tetrahydrofuran was distilled off under reduced pressure and the resulting residue was washed with ethyl acetate. The aqueous alkali layer was adjusted to pH 2 and extracted with ethyl acetate. The ethyl acetate layer was taken, washed with a saturated aqueous solution of sodium chloride and dried. Then, the solvent was distilled off under reduced pressure, whereupon a powdery residue was obtained. Following the addition of ether, the powder was collected by filtration and dried. By the above procedure there was obtained 0.114 g of the captioned compound.

IR(KBr, cm$^{-1}$): 1780

NMR(100 MHz, d$_6$-DMSO, δ): 2.05(s, CH$_3$), 3.43 & 3.66(ABq, J=18 Hz, 2-CH$_2$), 4.38 (s, ClCH$_2$), 4.70 & 5.02 (ABq, J=13 Hz, 3-CH$_2$), 5.17 (d, J=5 Hz, 6-H), 5.85(dd, J=5 & 8 Hz, 7-H), 7.37(s, thiazoline 5-H), 9.48(d, J=8 Hz, CONH), 11.58(br. s, =N—OH), 12.7 (br., thiazoline 3-H).

REFERENCE EXAMPLE 1

Production of 7-(4-bromo-3-oxobutyrylamino)-3-methyl-3-cephem-4-carboxylic acid

A solution of 2.2 g of diketene in 5 ml of methylene chloride was cooled to −40° C. and 4.4 g of bromine were added dropwise. Separately, 4.28 g of 7-aminodesacetoxycephalosporanic acid and 8.0 g of n-dibutylamine were dissolved in 120 ml of methylene chloride and cooled. The above reaction mixture was added dropwise to this mixed solution. The temperature of the mixture was increased to room temperature over 30 minutes, after which the mixture was stirred for an additional 30 minutes. The solvent was distilled off under reduced pressure and the resulting residue was shaken vigorously with 200 ml of ethyl acetate and 40 ml of 40% phosphoric acid. The organic layer was taken, washed with water, dried and concentrated to dryness under reduced pressure. To the residue was added ethyl ether, followed by stirring. The resultant powder was collected by filtration and dried. By the above procedure there were obtained 3.7 g of the captioned compound.

REFERENCE EXAMPLE 2

Production of 7-(4-bromo-3-oxobutyrylamino)-3-(mandelyloxymethyl)-3-cephem-4-carboxylic acid A solution of 1.34 g (0.013 mol) of diketene in 10 ml of methylene chloride was cooled to −30° C. and a solution of 3.14 g (0.014 mol) of bromine in 10 ml of methylene chloride was added dropwise. Separately, 3.6 g (0.01 mol) of 7-amino-3-(mandelyloxymethyl)-3-cephem-4-carboxylic acid and 2.8 ml (0.02 mol) of triethylamine were dissolved in 50 ml of methylene chloride and cooled to −20° C. The above reaction mixture was added dropwise to this mixed solution over a period of 10 minutes, after which the cooling apparatus was removed. After the mixture had warmed to room temperature, it was stirred for 30 minutes. The methylene chloride was distilled off under reduced pressure and the resulting residue was shaken vigorously with 30 ml of 10% phosphoric acid, 100 ml of water, 20 ml of tetrahydrofuran and 250 ml of ethyl acetate. The organic layer was taken, washed with water, dried and distilled under reduced pressure to remove the solvent. To the residue there were added 200 ml of ether and the vessel wall was scratched, whereupon 4.5 g of powder of the captioned compound were obtained.

IR(KBr, cm$^{-1}$): 3370, 1782, 1736, 1672, 1648, 1539

NMR (100 MHz, d$_6$-DMSO, δ): 3.24(br. s, 2-CH$_2$), 3.63(s, CH$_2$CO), 4.89(s, BrCH$_2$—), 4.77 & 5.05(ABq, J=14 Hz, 3-CH$_2$), 5.04(d, J=5 Hz, 6-H), 5.17(s, $$-\overset{|}{C}H-),$$

5.08(dd, J=5 & 8 Hz, 7-H), 7.3–7.5 (m, C$_6$H$_5$—), 9.02(d, J=8 Hz, CONH)

REFERENCE EXAMPLE 3

Production of 7-(4-chloro-3-oxobutyrylamino)-3-(1-methyl-1H-tetrazol-5-yl)thiomethyl-3-cephem-4-carboxylic acid While a solution of 166.5 g (1.98 mols) of diketene in 830 ml of methylene chloride was stirred under cooling at an internal temperature of −25° to −30° C., 140 g (1.97 mols) of chlorine gas were introduced over a period of 100 minutes. Thereafter, the solution was further stirred at that temperature for 30 minutes. Separately, 500 g(1.52 mols) of 7-amino-3-(1-methyl-1H-tetrazol-5-yl)thiomethyl-3-cephem-4-carboxylic acid and 394 g (3.05 mols) of dibutylamine were dissolved in 3 l of methylene chloride and cooled to −10°-20° C. The above reaction mixture was added dropwise to this mixed solution over a period of 30 minutes, after which the mixture was stirred at the same temperature for 40 minutes. The reaction mixture was added to a mixture of 6 l of ethyl acetate and 6 l of 10% phosphoric acid. After intense stirring, the organic layer was taken, washed with water, dried and concentrated to dryness under reduced pressure. The resulting residue was loosened by the addition of ether. By the above procedure there were obtained 644 g of powder of the captioned compound.

IR(KBr, cm$^{-1}$): 1783, 1732, 1679

NMR (100 MHz, d$_6$-DMSO, δ): 3.57 & 3.79 (ABq, J=18 Hz, 2-CH$_2$), 3.56(s, COCH$_2$CO), 3.91(s, tetrazole-CH$_3$), 4.20 & 4.37(ABq, J=13 Hz, 3-CH$_2$),4.52(s, ClCH$_2$), 5.07(d, J=5 Hz, 6-H), 5.67(dd, J=5 & 8Hz, 7-H), 9.05(d, J=8 Hz, —CONH—)

REFERENCE EXAMPLE 4

Production of 7-(4-bromo-3-oxobutyrylamino)-3-(1-methyl-1H-tetrazol-5yl)thiomethyl-3-cephem-carboxylic acid A solution of 1.03 g (0.01 mol) of diketene in 5 ml of methylene chloride was cooled to −30° C. and a solution of 2.24 g (0.01 mol) of bromine in 5 ml of methylene chloride was added dropwise. Separately, 3.29 g (0.01 mol) of 7-amino-3-(1-methyl-1H-tetrazol-5-yl)thiometh-yl-3-cephem-4-carboxylic acid and 2.02 g of triethylamine were dissolved in 20 ml of methylene chloride and cooled to −20° C. The above reaction mixture was quickly added dropwise to this mixed solution, whereupon the liquid temperature reached 0° C. The liquid temperature was gradually increased to room temperature, at which point the mixture was stirred for 15 minutes. The reaction mixture was added to a mixture of 150 ml of ethyl acetate and 100 ml of 10% phosphoric acid, followed by intense stirring. The organic layer was washed with water, dried and concentrated under reduced pressure. The resulting residue was loosened with ether. By the above procedure there were obtained 4.1 g of powder of the captioned compound.

IR(KBr, cm$^{-1}$): 1780, 1725, 1674

NMR (100 MHz, d$_6$-DMSO, δ): 3.59 & 3.81 (ABq, J=18 Hz, 2-CH$_2$), 3.63(s, COCH$_2$CO), 3.93(s, tetrazole-CH$_3$), 4.21 & 4.38(ABq, J=13 Hz, 3-CH$_2$), 4.38(s, BrCH$_2$), 5.07(d, J=5 Hz, 6-H), 5.67 (dd, J=5 & 8 Hz, 7-H), 9.06(d, J=8 Hz, CONH)

REFERENCE EXAMPLE 5

Production of 7-(4-bromo-3-oxobutyrylamino)-3-carbamoyloxymeth-yl-3-cephem-4-carboxylic acid A solution of 0.101 g of diketene in 2 ml of methylene chloride was cooled to −30° C. and a solution of 0.208 g of bromine in 1.3 ml of carbon tetrachloride was added dropwise. Separately, 0.303 g of 7-amino-3-carbamoyloxymethyl-3-cephem-4-carboxylic acid and 0.303 g of triethylamine were dissolved in 4 ml of methylene chloride and cooled. The above reaction mixture was added dropwise to this mixed solution and, after the cooling apparatus was removed to let the liquid temperature increase to room temperature, was stirred for 30 minutes. The methylene chloride was distilled off under reduced pressure and the residue was shaken vigorously with 20 ml of 10% phosphoric acid, 30 ml of methyl ethyl ketone and 5 ml of a saturated aqueous solution of sodium chloride. The organic layer was taken, washed with 5 ml of a saturated aqueous solution of sodium chloride and dried. The solvent was removed under reduced pressure and, after the addition of 5 ml of ether to the residue, the vessel wall was scratched, whereupon the captioned compound was obtained as a powder. Yield 0.148 g.

IR(KBr, cm$^{-1}$): 3390, 3000, 1780, 1740, 1550, 1400, 1330

UV λmax(ε, in water): 262 nm (0.89×10$^4$)

NMR (100 MHz, d$_6$-DMSO,δ): 3.48 & 3.66 (ABq, J=18 Hz, 2-CH$_2$), 3.64(s, COCH$_2$CO), 4.40(s, BrCH$_2$), 4.64 & 4.93(ABq, J=13 Hz, 3-CH$_2$), 5.11(d, J=5Hz, 6-H), 5.68(dd, J=5 & 9 Hz, 7-H), 6.5 (br. s, OCONH$_2$), 9.04(d, j=9 Hz, CONH)

Elemental analysis: Calcd. for C$_{13}$H$_{14}$N$_3$O$_7$SBr: C, 35.79; H, 3.23; N, 9.61; Found: C, 35.84; H, 3.25; N, 8.26

REFERENCE EXAMPLE 6

Production of 7-(4-chloro-3-oxobutyrylamino)-3-(mandelyloxyme-thyl)-3-cephem-4-carboxylic acid A solution of 0.26 g (3 mM) of diketene in 3 ml of methylene chloride was cooled to −30° C. and a solution of 0.21 g(3 mM) of chlorine in 3 ml of methylene chloride was added dropwise. Separately, 1.09 g (3 mM) of 7-amino-3-(mandelyloxymethyl)-3-cephem-4-carboxylic acid and 0.84 ml (6 mM) of triethylamine were dissolved in 15 ml of methylene chloride and cooled to −20° C. The above reaction mixture was added dropwise to this mixed solution and, after the cooling apparatus was removed to let the liquid temperature increase to room temperature, the mixture was stirred for 30 minutes. The methylene chloride was distilled off under reduced pressure and the resulting residue was shaken vigorously with 10 ml of 10% phosphoric acid, 30 ml of water, 10 ml of tetrahydrofuran and 100 ml of ethyl acetate. The organic layer was taken, washed with water and dried. The solvent was removed under reduced pressure and, with the addition of 100 ml of ether to the residue, the vessel wall was scratched. By the above procedure there were obtained 1.20 g of powder of the captioned compound.

IR(KBr, cm$^{-1}$): 1784, 1741, 1668, 1538

NMR(100 MHz, d$_6$-DMSO, δ): 3.25(br. s, 2-CH$_2$), 3.58(s, COCH$_2$CO), 4.56 (s,ClCH$_2$—) 4.78 & 5.07(ABq, J=13 Hz, 3-CH$_2$), 5.06(d, J=5 Hz, 6-H), 5.18(s,

—CH—),
|

5.68(dd, J=5 & 8 Hz, 7-H), 7.3–7.5 (m, C$_6$H$_5$—), 9.02(d, J=8 Hz, —CONH—).

REFERENCE EXAMPLE 7

Production of 1-methoxymethyl-1H-tetrazole-5-thiol

A mixture of 3.2 g of sodium azide, 6 ml of ethanol and 16 ml of water was heated under reflux with stirring and a solution of 5.2 g of methoxymethyl isothiocyanate in 2 ml of ethanol was added dropwise. The mixture was refluxed for 45 minutes. The ethanol was then removed under reduced pressure and the residue was made acidic with 1N-hydrochloric acid and extracted with ethyl acetate. The extract was dried and concentrated to dryness and the resulting crystalline residue was stirred with n-hexane and filtered. The crystals were recrystallized from toluene. By the above procedure there were obtained 1.4 g of the captioned compound m.p. 80°–82° C.

IR(KBr, cm$^{-1}$): 1503, 1360, 1080

NMR(60 MHz, d$_6$-DMSO, δ): 3.36(s, CH$_3$), 5.48(s, CH$_2$)

Elemental analysis: Calcd. for C$_3$H$_6$N$_4$OS: C, 24.66; H, 4.14; N, 38.35; Found: C, 24.71; H, 4.06; N, 37.24

REFERENCE EXAMPLE 8

In the same manner as in Reference Example 7, sodium azide was reacted with the corresponding isothiocyanic acid esters to obtain the following exemplary 1-substituted-1H-tetrazole-5-thiol compounds.

(1) 1-(2-N,N-dimethylaminoethyl)-1H-tetrazole-5-thiol m.p. 217°–219° C. (recrystallized from aqueous ethanol)

NMR(60 MHz, D$_2$O+NaHCO$_3$, δ): 3.03(s, N(CH$_3$)$_2$), 3.58(t, CH$_2$), 4.70(t, CH$_2$)

(2) 1-Methylthiomethyl-1H-tetrazole-5-thiol

IR(KBr, cm$^{-1}$): 1495, 1351

NMR (60 MHz, d$_6$-DMSO, δ): 2.25(s, SCH$_3$), 5.35(s, CH$_2$), 10.1(br. s, tetrazole-NH)

REFERENCE EXAMPLE 9

Production of 1-N,N-dimethylcarbamoylmethyl-1H-tetrazole-5-thiol (1) A mixture of 6.84 g of glycine-N,N-dimethylamide, 9.38 ml of triethylamine and 150 ml of methylene chloride was stirred and 5.09 g of carbon disulfide and 9.51 g of methyl iodide were added in the order mentioned. The mixture was then stirred at room temperature for 1 hour. This reaction mixture was shaken vigorously with 200 ml of a 5% aqueous solution of phosphoric acid and the organic layer was taken, washed with water, dried and concentrated under reduced pressure. The resulting crystalline residue was stirred with n-hexane, recovered by filtration and dried. By the above procedure there were obtained 12.2 g of methyl 2-(N,N-dimethylcarbamoylmethyl)-dithiocarbamate.

IR(KBr, cm$^{-1}$): 1626, 1543

NMR(60 MHz, d$_6$-DMSO, δ): 2.62(s, CH$_3$S), 3.02(s, N(CH$_3$)$_2$), 4.42 (d, J=4 Hz, CH$_2$), 8.30(br. s, NH)

(2) A mixture of 10 g of methyl 2-(N,N-dimethylcarbamoylmethyl)dithiocarbamate, 3.7 g of sodium azide and 50 ml of ethanol was stirred at 80° C. for 6.5 hours. The reaction mixture was adjusted to pH 2.5 with 10% hydrochloric acid and concentrated to dryness under reduced pressure. The residue was extracted with 100 ml of methanol. The methanolic extract was treated with activated carbon, concentrated to dryness and the residual powder was recrystallized from water. By the above procedure there was obtained 6.7 g of the captioned compound m.p. 195°–198° C. (decomp.)

NMR (60 MHz, d$_6$-DMSO, δ): 2.87 & 3.07(each s, N(CH$_3$)$_2$), 5.21(s, CH$_2$CO)

Elemental analysis: Calcd. for C$_5$H$_7$N$_5$S: C, 32.07; H, 4.85; N, 37.41; Found: C, 32.11; H, 4.90; N, 37.74

REFERENCE EXAMPLE 10

Production of 1-(2-carboxyethyl)-1H-tetrazole-5-thiol (1) in 100 ml of methylene chloride there were suspended 10.6 g of β-alanine benzyl ester p-toluenesulfonate and, after stirring, 6.06 g of triethylamine and 2.38 g of carbon disulfide were added in the order mentioned. The mixture was stirred at room temperature for 40 minutes. Then, 4.26 g of methyl iodide were added and the mixture was further stirred at room temperature for 2 hours. This reaction mixture was washed with water, dried and concentrated to dryness under reduced pressure, whereby 8.3 g of methyl 2-(2-benzyloxycarbonylethyl)dithiocarbamate were obtained as an oily product.

IR(Neat, cm$^{-1}$): 3300, 1730

NMR (60 MHz, CDCl$_3$, δ): 2.57(s, CH$_3$S), 2.76(t, J=6 Hz, CH$_2$CO), 4.03(m, NHCH$_2$), 5.17(s, Ph-CH$_2$), 7.25(s, C$_6$H$_5$), 7.7(br. s, NH)

(2) A mixture of 8.3 g of methyl 2-(2-benzyloxycarbonylethyl)dithiocarbamate, 1.95 g of sodium azide, 10 ml of ethanol and 40 ml of water was stirred at 80° C. for 1 hour. After cooling, the reaction mixture was diluted with 100 ml of water and shaken with ethyl acetate. The water layer was taken, adjusted to pH 1 with 10% hydrochloric acid and extracted with ethyl acetate. The extract was washed with water, dried and concentrated to dryness under reduced pressure. By the above procedure there were obtained 3.84 g of 1-(2-benzyloxycarbonylethyl)-1H-tetrazole-5-thiol as an oily product IR(neat, cm$^{-1}$): 1725

NMR (60 MHz, CDCl$_3$, δ): 3.09(t, J=6 Hz, CH$_2$CO) 4.54 (t, J=6 Hz, tetrazole-CH$_2$), 5.15(s, Ph-CH$_2$), 7.33(s, C$_6$H$_5$—)

(3) A mixture of 3.84 g of 1-(2-benzyloxycarbonylethyl)-1H-tetrazole-5-thiol, 30 ml of tetrahydrofuran and 29 ml of 1 N-sodium hydroxide was allowed to stand at room temperature for 2 hours. The reaction mixture was washed with ethyl acetate and the water layer was adjusted to pH 1 with 10% hydrochloric acid and extracted with ethyl acetate. The extract was washed with an aqueous solution of sodium chloride, dried and concentrated to dryness. By the above procedure there were obtained 1.9 g of powder of the captioned compound.

IR(Nujol, cm$^{-1}$): 1708

NMR (60 MHz, d$_6$-DMSO, δ) 2.88(t, J=7 Hz, CH$_2$CO), 4.40(t, J=7 Hz, tetrazole-CH$_2$) 12.2 (br. s, NH & CO$_2$H)

REFERENCE EXAMPLE 11

Production of 1-(carbamoylmethyl)-1H-tetrazole-5-thiol

The reactions described in Reference Example 10 (1) and (2) were carried out using glycine benzyl ester p-toluenesulfonate in lieu of β-alanine benzyl ester p-toluenesulfonate to prepare 1-benzyloxycarbonylmethyl-1H-tetrazole-5-thiol, which was then converted with alcoholic ammonia into the captioned compound.

Reference Example 12

Production of 2-methoxymethyl-1,3,4-thiadiazole-5-thiol (1) A solution of 4.9 g of potassium hydroxide in 30 ml of methanol was stirred under ice-cooling and 8.56 g of methoxyacetyl hydrazide and 5.3 ml of carbon disulfide were added. The mixture was stirred under cooling for 30 minutes and, then, at room temperature for 30 minutes. The methanol was removed under reduced pressure and the residue was loosened with ethanol, whereby a crystalline powder was obtained. The powder was recovered by filtration and dried. By the above procedure there were obtained 10.5 g of potassium 3-(methoxyacetyl)dithiocarbazinate.

(2) In 40 ml of ice-cooled concentrated sulfuric acid there were dissolved 10.5 g of potassium 3-(methoxyacetyl) dithiocarbazinate and the solution was stirred under ice-cooling for 10 minutes. It was then poured over 150 g of ice and stirred, whereupon crystals separated out. These crystals were collected by filtration, washed with cold water and dried. By the above procedure there were obtained 4.8 g of the captioned compound.

NMR (60 MHz, CDCl$_3$, δ) 3.46(s, CH$_3$), 4.60(s, CH$_2$), 12.33(br. s, thiadiazole-NH) Elemental analysis: Calcd. for C$_4$H$_6$N$_2$S$_2$: C, 29.61; H, 3.73; N, 17.27; Found: C, 29.43; H, 3.98; N, 17.34

REFERENCE EXAMPLE 13

Production of 3-hydroxymethyl-4-methyl-1,2,4-triazole-5-thiol

A mixture of 9 g of glycolic acid hydrazide, 7.3 g of methyl isothiocyanate, 50 ml of methanol and 50 ml of ethanol was heated under reflux for 5 hours. Following the addition of 2.3 g of sodium metal, the mixture was further refluxed for 24 hours. The reaction mixture was concentrated under reduced pressure and the residue was dissolved in 150 ml of water and adjusted to pH 2.5 with phosphoric acid. The resultant crystals were collected by filtration and recrystallized from ethanol. By the above procedure there were obtained 5.2 g of the captioned compound. m.p. 199°–201° C.

NMR (60 MHz, d$_6$-DMSO, δ): 3.54(s, CH$_3$), 4.56(s, CH$_2$O)

Elemental analysis:
Calcd. for C$_4$H$_7$N$_3$O$_3$S: C, 33.08; H, 4.86; N, 28.94; Found: C, 32.99; H, 4.90; N, 28.65

REFERENCE EXAMPLE 14

Production of 3-carbamoyl-4-methyl-1,2,4-triazole-5-thiol

In 100 ml of ethanol there were dissolved 5.3 g of 4-methylthiosemicarbazide together with 5.9 g of ethyl oxaminate and 1.6 g of sodium metal and the solution was heated under reflux for 48 hours. After cooling, the reaction mixture was diluted with 100 ml of water and made acidic with phosphoric acid. The resultant crystals were collected by filtration and recrystallized from water. By the above procedure there were obtained 2.0 g of the captioned compound.

NMR (60 MHz, d$_6$-DMSO, δ): 3.67(s, CH$_3$), 7.90 & 8.13(each s, CONH$_2$), 3.30(s, SH), 12.5 (s, triazole-NH)

REFERENCE EXAMPLE 15

The functional groups of the nitrogen-containing heterocyclic thiols obtained in the above Reference Examples were each subjected to a chemical transformation reaction known per se to produce the following nitrogen-containing heterocylic thiols.

(1) 1-Carboxymethyl-1H-tetrazole-5-thiol

1-N,N-dimethylcarbamoylmethyl-1H-tetrazole-5-thiol was hydrolyzed with a solution of sodium hydroxide. m.p. 156°–160° C. (decomp.)

IR (KBr, cm$^{-1}$): 1713

NMR (60 MHz, d$_6$-DMSO, δ): 5.03(s, CH$_2$CO), 12.09(br. s, NH & —COOH)

(2) 1(2-Hydroxyethyl)-1H-tetrazole-5-thiol

1-Benzyloxycarbonylmethyl-1H-tetrazole-5-thiol was reduced with lithium aluminum hydride-tetrahydrofuran. m.p. 137°–139° C.

NMR (60 MHz, d$_6$-DMSO, δ): 3.8(m, CH$_2$O), 4.2(m, tetrazole-CH$_2$—)

(3) 2-(2-N,N-dimethylaminoethyl)-1,3,4-thiadiazole-5-thiol 2-(N,N-dimethylcarbamoylmethyl)-1,3,4-thiadiazole-5-thiol was reduced with boron hydride-tetrahydrofuran.

NMR (60 MHz, D$_2$O,δ): 2.47(s, N(CH$_3$)$_2$), 3.0–3.3(A$_2$B$_2$-pattern m.CH$_2$CH$_2$).

REFERENCE EXAMPLE 16

Production of benzhydryl 4-bromo-3-oxobutyrate

In 10.5 ml of methylene chloride there were dissolved 2.1 g of diketene, and at a temperature not exceeding −30° C., a solution of 4.0 g of bromine in 12.5 ml of methylene chloride was added dropwise to the solution with stirring. After the dropwise addition was completed, the mixture was maintained at 0° C. for 10 minutes. Separately, 3.68 g of benzhydrol were dissolved in 25 ml of methylene chloride, followed by addition of 2.02 g of triethylamine. Under stirring at a temperature not exceeding −30° C., the solution of bromoacetoacetyl bromide prepared above was added dropwise. After the dropwise addition, the mixture was stirred at 0° C. for 40 minutes, at the end of which time it was washed with water. After drying over magnesium sulfate the solvent was distilled off under reduced pressure, whereupon 6.99 g of benzhydryl 4-bromo-3-oxobutyrate there were obtained.

IR(cm$^{-1}$, Neat): 1743

NMR(60 MHz, CDCl$_3$, δ): 3.68(s, COCH$_2$CO), 3.87(s, BrCH$_2$), 6.82(s, CH), 7.21 (s, aromatic H)

REFERENCE EXAMPLE 17

Production of benzhydryl 4-bromo-2-hydroxyimino-3-oxobutyrate

In 30 ml of acetic acid there were dissolved 6.94 g of benzhydryl 4-bromo-3-oxobutyrate and, under ice-cooling and stirring, a solution of 1.588 g of sodium nitrite in 6 ml of water was added dropwise. The mixture was further stirred at that temperature for 20 minutes and, following addition of 60 ml of a saturated aqueous solution of sodium chloride, the mixture was extracted with ethyl acetate. The ethyl acetate layer was washed with a saturated aqueous solution of sodium chloride and dried over magnesium sulfate. The solvent was removed under reduced pressure to recover 7.56 g of the captioned compound.

IR(cm$^{-1}$, Neat): 1742

NMR(60 MHz, CDCl$_3$, δ): 4.29(s, BrCH$_2$), 7.19(s, CH), 7.34(s, aromatic H), 9.79 (br. s, N=OH)

REFERENCE EXAMPLE 18

Production of benzhydryl 2-acetoxyimino-4-bromo-3-oxobutyrate

To 50 ml of acetic anhydride there were added 26.2 g of benzhydryl 4-bromo-2-hydroxyimino-3-oxobutyrate and the mixture was stirred at room temperature for 100 minutes. The excess acetic anhydride and the acetic acid produced by the reaction were distilled off under reduced pressure. By the above procedure there were obtained 26.7 g of the captioned compound.

IR(cm$^{-1}$, Neat): 1809, 1750

NMR (60 MHz, CDCl$_3$,δ): 1.94(s, CH$_3$), 4.44(s, BrCH$_2$), 7.11(s, CH), 7.30(s, aromatic H)

REFERENCE EXAMPLE 19

Production of benzhydryl 2-acetoxyimino-2-(2-imino-4-thiazolin-4yl)acetate

In 20 ml of N,N-dimethylacetamide there were dissolved 26.5 g of benzhydryl 2-acetoxyimino-4-bromo-3-oxobutyrate and, under ice-cooling and stirring, 4.81 g of thiourea were added. The mixture was stirred at room temperature for 3 hours and 15 minutes, after which it was washed well with 80 ml of ether. The ether was discarded after being removed by decantation. The above procedure was carried out once again and the mixture was poured into 100 ml of water, whereupon crystals separated out. After loosening, the crystals were recovered by filtration and washed with ether, a small amount of ethyl acetate and ether in the order mentioned. By the above procedure there were obtained 10.738 g of crystals of the captioned compound.

IR(cm$^{-1}$, Nujol): 1790, 1746

NMR (100 MHz, d$_6$-DMSO,δ) 1.92(s, CH$_3$), 7.12 & 7.21 (each s, CH & thiazoline 5-H), 7.42 (m, aromatic H)

REFERENCE EXAMPLE 20

Production of benzhydryl 2-acetoxyimino-2-(2-chloroacetylimino-4-thiazolin-4-yl)acetate In 100 ml of N,N-dimethylformamide there were suspended 19.7 g of benzhydryl 2-acetoxyimino-2-(2-imino-4-thiazolin-4-yl)acetate, followed by the addition of 6.02 g of triethylamine. Under ice-cooling and stirring, 4.98 ml of chloroacetyl chloride were added dropwise. The mixture was further stirred at that temperature for 10 minutes and, then, at room temperature for 20 minutes. Thereafter, 1.50 ml of chloroacetyl chloride were added dropwise and the mixture was stirred for 20 minutes. The reaction mixture was poured into a solution of 4.4 g of sodium hydrogen carbonate in 200 ml of water and extracted with 500 ml of ethyl acetate in three installments. The ethyl acetate layers were pooled, washed twice with 100 ml of a 1% solution of sodium hydrogen carbonate and further washed with a saturated aqueous solution of sodium chloride. The drying with magnesium sulfate and the decolorization with activated carbon were concurrently carried out and, after filtering, the solvent was distilled off. To the residue there were added 20 ml of ethyl acetate and the mixture was allowed to stand. The resultant crystals were recovered by filtration and dried. By the above procedure there were obtained 12.7 g of benzyhydryl 2-acetoxyimino-2-(2-chloroacetylimino-4-thiazolin-4-yl) acetate (syn-isomer). This product contained a small amount of anti-isomer, which was removed by the following procedure.

In 50 ml of tetrahydrofuran there were dissolved 12.0 g of the above crude crystals and, following the addition of 100 ml of ethyl acetate, the mixture was filtered. The filtrate was distilled under reduced pressure to remove the solvent and 20 ml of ethyl acetate were added to the residue. The resultant crystals were collected by filtration and dried. By the above procedure there were obtained 8.142 g of benzhydryl 2-acetoxyimino-2-(2-chloroacetylimino-4-thiazolin-4-yl)acetate(syn-isomer).

IR(cm$^{-1}$, Nujol): 1760, 1747, 1550

NMR(100 MHz, d$_6$-DMSO, δ) 1.93(s, CH$_3$), 4.41(s, ClCH$_2$), 7.18(s, CH), 7.2–7.6 (m,aromatic H), 7.90(s, thiazoline 5-H), 12.90(br. s,NH)

Elemental analysis: Calcd. for C$_{22}$H$_{18}$ClN$_3$O$_5$S; C, 55.90; H, 3.84; N, 8.90; Found: C, 56.19; H, 3.83; N, 8.84

REFERENCE EXAMPLE 21

In 16.5 ml of anisole there were suspended 6.10 g of benzhydryl 2-acetoxyimino-2-(2-chloroacetylimino-4-thiazolin-4-yl)acetate(syn-isomer) and under ice-cooling and stirring, 65.7 ml of trifluoroacetic acid was added dropwise. The mixture were stirred at that temperature for 15 minutes, after which the trifluoroacetic acid was distilled off under reduced pressure. To the residue was added n-hexane, whereupon an oily product separated out. The product was washed well with n-hexane ad the n-hexane was discarded after being removed by decantation. This procedure was carried out once again. To the oily residue was added ether, whereupon a crystalline powder separated out. Following the addition of a small amount of ether, the crystalline powder was collected by filtration, washed with a small amount of ether and dried. By the above procedure there were obtained 3.125 g of 2-acetoxyimino-2-(2-chloroacetylimino-4-thiazolin-4-yl)-acetic acid (syn-isomer).

IR(cm$^{-1}$, Nujol): 1792, 1694

NMR (100 MHz, d$_6$-DMSO, δ): 2.22(s,CH$_3$), 4.41(s, ClCH$_2$), 7.90(s, thiazoline 5-H), 12.95(br. s, NH)

Elemental analysis: Calcd. for C$_9$H$_8$ClN$_3$O$_5$S; C, 35.36; H, 2.64; N, 13.75; Found: C, 35.30; H, 2.64; N, 13.75

What is claimed is:

1. A 2-(syn)-hydroxyimino-acetamide compound of the formula:

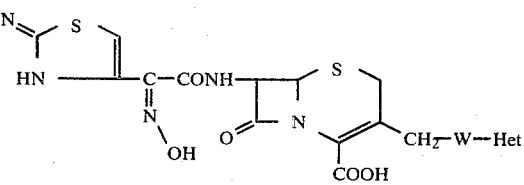

wherein W is sulfur; Het is substituted or unsubstituted heterocyclic; said heterocyclic is pyridyl, N-oxopyridyl, pyrimidyl, pyridazinyl, N-oxopyridazinyl, pyrazolyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2-H-tetrazolyl, or a pharmaceutically acceptable salt or ester thereof; when Het is substituted, the substituent is alkyl of one to four carbon atoms, haloalkyl of one to four carbon atoms, alkoxy of one to four carbon atoms, halogen, hydroxyl, mercapto, amino, carboxyl, carbamoyl, a group of the formula: —X—Z$^1$ in which X is an alkylene of one to four carbon atoms and Z$^1$ is hydroxyl, mercapto, amino, a mono- or di-alkylamino of which the alkyl has one to four carbon atoms, guanyl, carboxyl, sulfo, carbamoyl, an alkoxycarbonyl of which the alkyl has one to four carbon atoms, a mono- or di-alkylcarbamoyl of which alkyl has one to four carbon atoms, an alkoxy of one to four carbon atoms, an alkylthio of which alkyl has one to four carbon atoms, an alkylsulfonyl of which alkyl has one to four carbon atoms or an alkylcarbonyloxy of which alkyl has one to four carbon atoms, a group of the formula: —S—Z$^2$ in which Z$^2$ is an alkyl of one to four carbon atoms or the group —X—Z¹, or the substituent is a group of the formula:

in which each of $Z^3$ and $Z^4$ is an alkyl of one to four carbon atoms, the group —X—Z¹, an alkoxycarbonyl of which alkoxy has one to four carbon atoms, an alkylcarbonyl of which alkyl has one to four carbon atoms, carbamoyl or a mono- or di-alkylcarbamoyl of which alkyl has one to four carbon atoms.

2. A compound as claimed in claim 1, wherein W—Het is a 5- or 6-membered heterocyclic thio

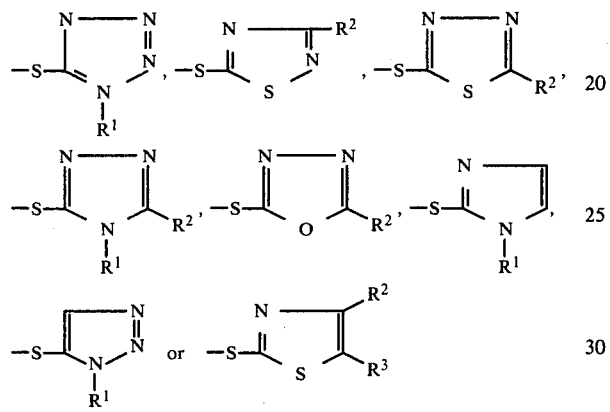

wherein $R^1$ is hydrogen or a residue of the formula: —(CH₂)ₙP, and each of $R^2$ and $R^3$ is hydrogen, amino, carbamoyl, a residue of the formula: —NHCOOR⁷(in which $R^7$ is an alkyl), a residue of the formula: —S—(CH₂)ₙQ (in which n is an integer from 1 to 3 and Q is carboxyl, hydroxyl, hydrogen or sulfo) or a residue of the formula: —(CH₂)ₙP(in which each of n and P has the same meaning as defined above).

3. A compound as claimed in claim 1, wherein W—Het— is 1-substituted-1H-tetrazol-5-ylthio, 2-substituted-1,3,4-thiadiazol-5-ylthio, 3,4-disubstituted-1,2,4-triazol-5-ylthio or 4- substituted-thiazol-2-ylthio, the substituent being methyl, carboxymethyl, hydroxymethyl, hydroxyethyl, carbamoylmethyl or 2-N,N-dimethylaminoethyl, the two substituents of 3,4-disubstituted-1,2,4-triazol-5-ylthio being same or different.

4. A compound as claimed in claim 1, wherein W—Het— is 3-substituted-1,2,4-thiadiazol-5-ylthio, 2-substituted-1,3,4-oxadiazol-5-ylthio, 1-substituted-imidazol-2-ylthio, 1-substituted-1H-tetrazol-5-ylthio, 2-substituted-1,3,4-thiadiazol-5-ylthio, 3,4-disubstituted-1,2,4-triazol-5-ylthio or 4-substituted-thiazol-2-ylthio, the substituent being methyl, carboxymethyl, hydroxymethyl, hydroxyethyl, carbamoylmethyl, 2-N,N-dimethylaminoethyl, methoxymethyl or ethoxycarbonylmethyl, the two substituents of 3,4-disubstituted-1,2,4-triazol-5-ylthio being same or different.

5. A compound as claimed in claim 1, wherein the ester is an alkoxymethyl ester, an alkoxyethyl ester, an alkylthiomethyl ester, an alkylcarbonyloxymethyl ester or an alkoxycarbonyloxyalkyl ester.

6. A compound as claimed in claim 1, wherein the ester is methoxyethyl ester, ethoxymethyl ester, isopropoxymethyl ester, α-methyoxyethyl ester, α-ethoxyethyl ester, ethylthiomethyl ester, isopropylthiomethyl ester, pivaloyloxymethyl ester, α-acetoxybutyl ester or 1-(ethoxycarbonyloxy)ethyl ester.

7. A compound as claimed in claim 1, wherein the ester is pivaloyloxymethyl ester or 1-(ethoxycarbonyloxy)ethyl ester and W-Het is a residue of the formula:

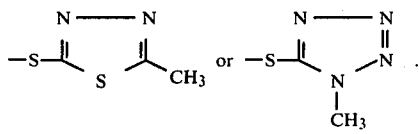

8. A compound as claimed in claim 1, namely 7-[2-(2-imino-4-thiazolin-4-yl)-2-hydroximino-acetamido]-3-(1-methyltetrazol-5-yl)thiomethyl-3-cephem-4-carboxylic acid (syn-isomer) or a pharmaceutically acceptable salt thereof.

9. A compound as claimed in claim 1, namely 7-[2-(2-imino-4-thiazolin-4-yl)-2-hydroxyimino-acetamido]-3-[1-(2-N,N-dimethylaminoethyl)tetrazol-5-yl]thiomethyl-3-cephem-4-carboxylic acid (syn-isomer) or a pharmaceutically acceptable salt thereof.

10. A compound as claimd in claim 1, namely 7[2-(2-imino-4-thiazolin-4-yl)-2-hydroxyimino-acetamido]-3-[1-(3-N,N-dimethylaminopropyl)tetrazol-5-yl]thiomethyl-3-cephem-4-carboxylic acid (syn-isomer) or a pharmaceutically acceptable salt thereof.

11. A compound as claimd in claim 1, namely 7-[2-(2-imino-4-thiazolin-4-yl)-2-hydroxyimino-acetamido]-3-(1-carbamoylmethyltetrazol-5-yl)thiomethyl-3-cephem-4-carboxylic acid (syn-isomer) or a pharmaceutically acceptable salt thereof.

12. A compound as claimed in claim 1, namely 7-[2-(2-imino-4-thiazolin-4-yl)-2-hydroxyimino-acetamido]-3-[1-(2-hydroxyethyl)tetrazol-5-yl]thiomethyl-3-cephem-4-carboxylic acid (syn-isomer) or a pharmaceutically acceptable salt thereof.

13. A compound as claimed in claim 1, namely 7-[2-(2-imino-4-thiazolin-4-yl)-2-hydroxyimino-acetamido]-3-(1,3,4-thiadiazol-2-yl)thiomethyl-3-cephem-4-carboxylic acid (syn-isomer) or a pharmaceutically acceptable salt thereof.

14. A compound as claimed in claim 1, namely 7-[2-(2-imino-4-thiazolin-4-yl)-2-hydroxyimino- acetamido]-3-(2-methyl-1,3,4-thiadiazol-5-yl)thiomethyl-3-cephem-4-carboxylic acid (syn-isomer) or a pharmaceutically acceptable salt thereof.

15. A compound as claimed in claim 1, namely 7-[2-(2-imino-4-thiazolin-4-yl)-2-hydroxyimino-acetamido]-3-[2-(2-N,N-dimethylaminoethyl)-1,3,4-thiadiazol-5-yl]thiomethyl-3-cephem-4-carboxylic acid (syn-isomer) or a pharmaceutically acceptable salt thereof.

16. A compound as claimed in claim 1, namely 7-[2-(2-imino-4-thiazolin-4-yl)-2-hydroxyimino-acetamido]-3-(2-hydroxymethyl-1,3,4-thiadiazol-5-yl)thiomethyl-3-cephem-4-carboxylic acid (syn-isomer) or a pharmaceutically acceptable salt thereof.

17. A compound as claimed in claim 1, namely 7-[2-(2-imino-4-thiazolin-4-yl)-2-hydroxyimino-acetamido]-3-(2-N,N-dimethylcarbamoylmethyl-1,3,4-thiadiazol-5-yl)thiomethyl-3-cephem-4-carboxylic acid (syn-isomer) or a pharmaceutically acceptable salt thereof.

18. A compound as claimed in claim 1, namely 7[2-(2-imino-4-thiazolin-4-yl)-2-hydroxyimino-acetamido]-3-[2-(2-hydroxyethylthio-1,3,4-thiadiazol-5-yl]thiomethyl-3-cephem-4-carboxylic acid (syn- isomer) or a pharmaceutically acceptable salt thereof.

19. A compound as claimed in claim 1, namely 7-[2-(2-imino-4-thiazolin-4-yl)-2-hydroxyimino-acetamido]-3-(2-carboxymethyl-1,3,4-thiadiazol-5-yl)-thiomethyl-3-cephem-4-carboxylic acid (syn-isomer) or a pharmaceutically acceptable salt thereof.

20. A compound as claimed in claim 1, namely 7-[2-(2-imino-4-thiazolin-4-yl)-2-hydroxyimino-acetamido]-3-(3-methyl-1,2,4-thiadiazol-5-yl)thiomethyl-3-cephem-4-carboxylic acid (syn-isomer) or a pharmaceutically acceptable salt thereof.

21. A compound as claimed in claim 1, namely 7-[2-(2-imino-4-thiazolin-4-yl)-2-hydroxyimino-acetamido]-3-(1,2,3-triazol-4-yl)thiomethyl-3-cephem-4-carboxylic acid (syn-isomer) or a pharmaceutically acceptable salt thereof.

22. A compound as claimed in claim 1, namely 7-[2-(2-imino-4-thiazolin-4-yl)-2-hydroxyimino-acetamido]-3-(4-methyl-1,2,4-triazol-3-yl)thiomethyl-3-cephem-4-carboxylic acid (syn-isomer) or a pharmaceutically acceptable salt thereof.

23. A compound as claimed in claim 1, namely 7-[2-(2-imino-4-thiazolin-4-yl)-2-hydroxyimino-acetamido]-3-(3,4-dimethyl-1,2,4-triazol-5-yl)thiomethyl-3-cephem-4-carboxylic acid (syn-isomer) or a pharmaceutically acceptable salt thereof.

24. A compound as claimed in claim 1, namely 7-[2(2-imino-4-thiazolin-4-yl)-2-hydroxyimino-acetamido]-3-(3-hydroxymethyl-4-methyl-1,2,4-triazol-5-yl)thiomethyl-3-cephem-4-carboxylic acid (syn-isomer) or a pharmaceutically acceptable salt thereof.

25. A compound as claimed in claim 1, namely b 7-[2-(2-imino-4-thiazolin-4-yl)-2-hydroxyimino-acetamido]-3-(2-methyl-1,3,4-oxadiazol-5-yl)thiomethyl-3-cephem-4-carboxylic acid (syn-isomer) or a pharmaceutically acceptable salt thereof.

26. A compound as claimed in claim 1, namely 7[2-(2-imino-4-thiazolin-4-yl)-2-hydroxyimino-acetamido]-3-(4-carboxymethylthiazol-2-yl)-thiomethyl-3-cephem-4-carboxylic acid (syn-isomer) or a pharmaceutically acceptable salt thereof.

27. A compound as claimed in claim 1, namely 7-[2-(2-imino-4-thiazolin-4-yl)-2-hydroxyimino-acetamido]-3-(2-methoxymethyl-1,3,4-thiadiazol-5-yl)thiomethyl-3-cephem-4-carboxylic acid (syn-isomer) or a pharmaceutically acceptable salt thereof.

28. A compound as claimed in claim 1, namely 7[2-(2-imino-4-thiazolin-4-yl)-2-hydroxyimino-acetamido]-3-[2-(2-hydroxyethyl)-1,3,4-thiadiazol-5-yl]thiomethyl-3-cephem-4-carboxylic acid (syn-isomer) or a pharmaceutically acceptable salt thereof.

29. A compound as claimed in claim 1, namely 7[2-(2-imino-4-thiazolin-4-yl)-2-hydroxyimino-acetamido]-3-(2-ethoxycarbonylmethyl-1,3,4-thiadiazol-5-yl)thiomethyl-3-cephem-4-carboxylic acid (syn-isomer) or a pharmaceutically acceptable salt thereof.

30. A compound as claimed in claim 1, namely pivaloyloxymethyl 7-[2-(2-imino-4-thiazolin-4-yl)-2-hydroxyimino-acetamido]-3-(1-methyl-1H-tetrazol-5-yl)-thiomethyl-3-cephem-4-carboxylate (syn-isomer) or a pharmaceutically acceptable salt thereof.

31. A compound as claimed in claim 1, namely pivaloyloxymethyl 7-[2-(2-imino-4-thioazolin-4-yl)-2-hydroxyimino-acetamido]-3-(2-methyl-1,3,4-thiadiazol-5-yl)thiomethyl-3-cephem-4-carboxylate (syn-isomer) or a pharmaceutically acceptable salt thereof.

32. An antimicrobial composition containing a therapeutically effective amount of a compound according to claim 1 and at least one pharmaceutically acceptable carrier.

33. A method of treating a gram-positive or gram-negative bacterial infection comrpising internally administering to an infected animal a therapeutically effective amount of a compound as claimed in claim 1.

* * * * *

UNITED STATES PATENT AND TRADEMARK OFFICE
CERTIFICATE OF CORRECTION

PATENT NO. : 4,264,595
DATED : Apr. 28, 1981
INVENTOR(S) : Mitsuo Numata, et al

It is certified that error appears in the above—identified patent and that said Letters Patent is hereby corrected as shown below:

Column 6, line 30: the chemical formula " 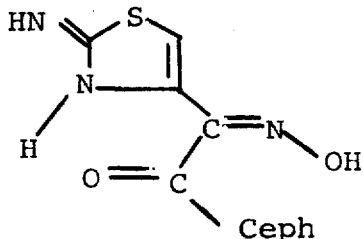 "

should read 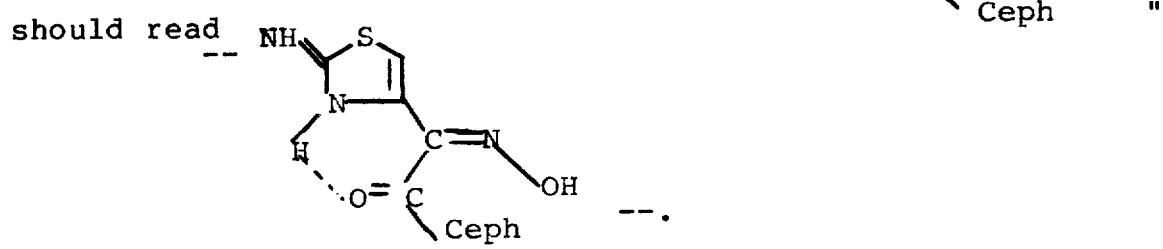 --.

Column 7, line 39: "3-[2-82" should read -- 3-[2-(2 --.

Column 8, line 37: "compound [I] of" should should read -- compounds [I] or --.

Column 8, line 54: "salt" should read -- salts --.

Column 9, line 54: "hydroxide) potassium" should read -- hydroxide, potassium --.

Column 14, line 7: "when syn" should read -- when a syn --.

Column 19, line 33: "that were" should read -- there were --.

Column 29, line 22: "[2-(imino-" should read -- [2-(2-imino --.

UNITED STATES PATENT AND TRADEMARK OFFICE
CERTIFICATE OF CORRECTION

PATENT NO. : 4,264,595
DATED : Apr. 28, 1981
INVENTOR(S) : Mitsuo Numata, et al

It is certified that error appears in the above—identified patent and that said Letters Patent is hereby corrected as shown below:

Column 30, line 20: "was added" should read -- were added --.

"3-CH),3.42),342 &" should read -- 3-CH$_3$, 3.42 & --

Column 36, compound No. 13: "(100NHz" should read -- (100MHz --.

Column 36, compound No. 17: "(100NHz" should read -- (100MHz --.

Column 38, compound No. 25: "3.3-4.0(xH)" should read -- 3.3-4.0(m,4xH) --.

Signed and Sealed this

Ninth Day of April 1985

[SEAL]

Attest:

DONALD J. QUIGG

Attesting Officer

Acting Commissioner of Patents and Trademarks